Figure 1A:
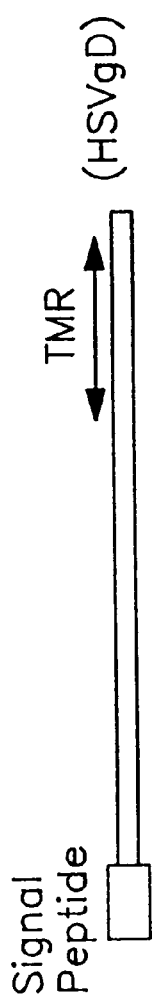

US005958895A

United States Patent [19]

Pachuk et al.

[11] Patent Number: 5,958,895
[45] Date of Patent: Sep. 28, 1999

[54] DNA VACCINES FOR HERPES SIMPLEX VIRUS

[75] Inventors: Catherine Pachuk, Lansdale; Kathleen Herold, Philadelphia, both of Pa.

[73] Assignee: American Home Products Corporation, Madison, N.J.

[21] Appl. No.: 08/956,998

[22] Filed: Oct. 23, 1997

Related U.S. Application Data

[60] Provisional application No. 60/028,754, Oct. 23, 1996, abandoned, and provisional application No. 60/053,206, Jul. 21, 1997, abandoned.

[51] Int. Cl.⁶ .................................................. A61K 48/00
[52] U.S. Cl. ............................ 514/44; 530/395; 536/231; 536/23.72; 424/186.1; 424/229.1
[58] Field of Search .............................. 536/23.1, 23.72; 435/320.1; 514/44; 530/395; 424/186.1, 299.1

[56] References Cited

U.S. PATENT DOCUMENTS

| 5,612,041 | 3/1997 | Burke et al. ......................... 424/231.1 |
| 5,654,174 | 8/1997 | Cohen et al. ........................... 435/69.3 |

OTHER PUBLICATIONS

Z. Xiang et al, "Immune Responses to Nucleic Acid Vaccines to Rabies Virus", *Virology*, 209:569–579 (1995).

G. Inchauspe et al, "Immune Responses Against Hepatitis C Virus Structural Proteins Following Genetic Immunisation", *Dev. Biol. Stand.*, 92:163–168 (1998).

G. Inchauspe et al, "Plasmid DNA Expressing a Secreted or a Nonsecreted Form of Hepatitis C Virus Nucleocapsid: Comparative Studies of Antibody and T–Helper Responses Following Genetic Immunization", *DNA and Cell Biol.*, 16(2):185–195 (1997).

R. Johnson et al, "Herpes Simplex Virus Glycoprotein D is Recognized as Antigen by CD4+ and CD8+ T Lymphocytes from Infected Mice", *J. Immunol.*, 145(2):702–710 (Jul. 15, 1990).

H. Ghiasi et al, "Expression of Seven Herpes Simplex Virus Type 1 Glycoproteins (gB, gC, gE, gG, and gI): Comparative Protection Against Lethal Challenge in Mice", *J. Virol.*, 68(4):2118–2126 (Apr. 1994).

G. Inchauspe et al, "Plasmid DNA Expressing a Secreted or a Nonsecreted Form of Hepatitis C Virus Nucleocapsid: Comparative Studies of Anitbody and T–Helper Responses Following Gentic Immunization", *DNA Cell Biol.*, 16(2):185–195 (Feb. 1997)(Abstract only).

Z. Xiang et al, "Immune Responses to Nucleic Acid accines to Rabies Virus", *Virology*, 209(2):569–579 (Jun. 1, 1995)(Abstract only).

PCT International Search Report, Mailed Mar. 4, 1998, 4 pages.

Cohen, Gary H. et al., "Expression of Herpes Simplex Virus Type 1 Glycoprotein D Deletion Mutants in Mammalian Cells," Journal of Virology, Jun. 1988, vol. 62, No. 8, pp. 1932–1940.

Chiang, Hsien–Yuan et al., "Identification of Functional Regions of Herpes Simplex Virus Glycoprotein gD by Using Linker–Insertion Mutagensis," Journal of Virology, Apr. 1994, vol. 68, No. 4 pp. 2529–2543.

Nicola, Anthony V. et al., "Structure–Function Analysis of Soluble Forms of Herpes Simplex Virus Glycoprotein D," Journal of Virology, Jun. 1996, vol. 70, No. 6, pp. 3815–3822.

Berman et al. The Journal of Infectious Diseases. vol., 157, pp. 897–901, May 1988.

Lasky et al. Bio/Technology. pp. 527–532, Jun. 1984.

Watson, R.J. Gene. vol. 26, pp. 307–312, 1983.

Orkin et al. Report and Recommendations of the Panel to assess the NIH investment in research on gene therapy, Dec. 1995.

Crystal, R. Science. vol. 270, pp. 404–410, 1995.

Berman et al. Science. vol. 227, pp. 1490–1492, Mar. 1985.

Yokoyama et al. FEMS Immunology and Medical Microbiology. vol. 14, pp. 221–230, 1996.

Chattergoon et al. The FASEB Journal. vol. 11, pp. 753–763, Aug. 1997.

Webster et al. Biodrugs. vol. 4, pp. 273–292, Oct. 1997.

*Primary Examiner*—James Ketter
*Assistant Examiner*—Irem Yucel
*Attorney, Agent, or Firm*—Howson and Howson

[57] ABSTRACT

Protective and therapeutic vaccines are disclosed. Vaccines for preventing or treating herpes simplex virus infection are disclosed. Methods for preventing herpes simplex virus infection and treating individuals who have been infected with herpes simplex virus and to compositions for and methods of making prophylactic and therapeutic vaccines for herpes simplex virus are disclosed.

34 Claims, 17 Drawing Sheets

```
DOCUMENT ID  330268      1635 BP DS- DNA     LINEAR   Update: 2/16/87
DEFINITION   Herpes simplex virus type 2  (HSV-2) glycoprotein D  (gD-2)
             gene and flanks.
KEYWORDS     glycoprotein, glycoprotein D
SOURCE       Herpes simplex virus type 2
  ORGANISM   Viridae; ds-DNA enveloped viruses; Herpesviridae;
             Alphaherpesvirinae.
ORIGIN       423 bp upstream of PvuII site.
REFERENCE    [1]  Medline ID  [84159516]
  AUTHORS    Watson, R.J.
  TITLE      DNA sequence of the Herpes simplex virus type 2
             glycoprotein D gene
  JOURNAL    Gene,  26,  307-312,    (1983)

COMMENT      Database Reference:
               GENBANK    HS2GD
               Accession:  K01408
             ------------
             [1] compared the amino acid sequences of the gD-1 and gD-
             2 genes and found them 86% homologous.
             GenBank Division:  VRL FEATURES        From  To/Span      Description
    pept         268     1449      glycoprotein D-2
    mRNA         199  >  1449      gD-2 mRNA
    sigp         268      342      sig_peptide; glycoprotein D-2 signal
             peptide;  /codon_start=1
    matp         343     1446      mat_peptide; glycoprotein D-2 mature
             peptide; /codon_start=1
    ????           1     1635      source; /organism-Herpes simplex
             virus type 2
```

FIG. 2A

```
         10         20         30         40         50
                                                      *
cttgggggggg ggggggaaga aactaaaaac acatcaagcc cacaacccat
gaaccccccc ccccccttct ttgattttttg tgtagttcgg gtgttgggta 60         70         80         90        100
                                                      *
cccacaaggg gggttatggc ggacccaccg caccaccata ctccgattcg
gggtgttccc cccaataccg cctgggtggc gtggtggtat gaggctaagc 110        120        130        140        150
                                                      *
accacatatg caaccaaatc accccagag gggaggttcc attttttacga
tggtgtatac gttggtttag tggggtctc ccctccaagg taaaaatgct 160        170        180        190        200
                                                      *
ggaggaggag tataatagag tctttgtgtt taaaacccgg ggtcggtgtg
cctcctcctc atattatctc agaaacacaa attttgggcc ccagccacac
                                                    —>

210        220        230        240        250
                                                      *
gtgttcggtc ataagctgca ttgcgaacca ctagtcgccg tttttcgtgt
cacaagccag tattcgacgt aacgcttggt gatcagcggc aaaaagcaca
        a          GD-2 MRNA_a          a            —>

260        270        280        290        300
                                                      *
gcatcgcgta tcacggcatg gggcgtttga cctccggcgt cgggacggcg
cgtagcgcat agtgccgtac cccgcaaact ggaggccgca gccctgccgc
        a          GD-2 MRNA_a          a            —>

310        320        330        340        350
                                                      *
gccctgctag ttgtcgcggt gggactccgc gtcgtatgcg ccaaatacgc
cgggacgatc aacagcgcca ccctgaggcg cagcagacgc ggtttatgcg
        a          GD-2 MRNA_a          a            —>

360        370        380        390        400
                                                      *
cttagcagac ccctcgctta agatggccga tcccaatcga tttcgcggga
gaatcgtctg gggagcgaat tctaccggct agggttagct aaagcgccct
        a          GD-2 MRNA_a          a            —>

410        420        430        440        450
                                                      *
agaaccttcc ggttttggac cagctgaccg acccccccgg ggtgaagcgt
tcttggaagg ccaaaacctg gtcgactggc tggggggcc ccacttcgca
        a          GD-2 MRNA_a          a            —>
```

FIG. 2B

```
         460        470        480        490        500
                                                       *
gtttaccaca ttcagccgag cctggaggac ccgttccagc cccccagcat
caaatggtgt aagtcggctc ggacctcctg ggcaaggtcg ggggtcgta
_____a_____GD-2 MRNA_a_____a_____>

510        520        530        540        550
                                                       *
cccgatcact gtgtactacg cagtgctgga acgtgcctgc cgcagcgtgc
gggctagtga cacatgatgc gtcacgacct tgcacggacg gcgtcgcacg
_____a_____GD-2 MRNA_a_____a_____>

560        570        580        590        600
                                                       *
tcctacatgc cccatcggag gccccccaga tcgtgcgcgg ggcttcggac
aggatgtacg gggtagcctc cggggggtct agcacgagcc ccgaagcctg
_____a_____GD-2 MRNA_a_____a_____>

610        620        630        640        650
                                                       *
gaggcccgaa agcacacgta caacctgacc atcgcctggt atcgcatggg
ctccgggctt tcgtgtgcat gttggactgg tagcggacca tagcgtaccc
_____a_____GD-2 MRNA_a_____a_____>

660        670        680        690        700
                                                       *
agacaattgc gctatcccca tcacggttat ggaatacacc gagtgcccct
tctgttaacg cgatagggt agtgccaata ccttatgtgg ctcacgggga
_____a_____GD-2 MRNA_a_____a_____>

710        720        730        740        750
                                                       *
acaacaagtc gttggggtc tgccccatcc gaacgcagcc ccgctggagc
tgttgttcag caaccccag acggggtagg cttgcgtcgg ggcgacctcg
_____a_____GD-2 MRNA_a_____a_____>

760        770        780        790        800
                                                       *
tactatgaca gctttagcgc cgtcagcgag gataacctgg gattcctgat
atgatactgt cgaaatcgcg gcagtcgctc ctattggacc ctaaggacta
_____a_____GD-2 MRNA_a_____a_____>

810        820        830        840        850
                                                       *
gcacgccccc gccttcgaga ccgcgggtac gtacctgcgg ctagtgaaga
cgtgcggggg cggaagctct ggcgcccatg catggacgcc gatcacttct
_____a_____GD-2 MRNA_a_____a_____>

860        870        880        890        900
                                                       *
taaacgactg gacggagatc acacaattta tcctggagca ccgggcccgc
atttgctgac ctgcctctag tgtgttaaat aggacctcgt ggcccgggcg
_____a_____GD-2 MRNA_a_____a_____>
```

FIG. 2C

```
         910         920         930         940          950
                                                             *
gcctcctgca agtacgctct cccccctgcgc atccccccgg cagcgtgcct
cggaggacgt tcatgcgaga gggggacgcg taggggggcc gtcgcacgga
_____a_____GD-2 MRNA_a_____a_____>

960         970         980         990         1000
                                                             *
cacctcgaag gcctaccaac agggcgtgac ggtcgacagc atcgggatgt
gtggagcttc cggatggttg tcccgcactg ccagctgtcg tagccctaca
_____a_____GD-2 MRNA_a_____a_____>

1010        1020        1030        1040         1050
                                                             *
taccccgctt tatccccgaa aaccagcgca ccgtcgccct atacagctta
atggggcgaa ataggggctt ttggtcgcgt ggcagcggga tatgtcgaat
_____a_____GD-2 MRNA_a_____a_____>

1060        1070        1080        1090         1100
                                                             *
aaaatcgccg ggtggcacgg ccccaagccc ccgtacacca gcaccctgct
ttttagcggc ccaccgtgcc ggggttcggg ggcatgtggt cgtgggacga
_____a_____GD-2 MRNA_a_____a_____>

1110        1120        1130        1140         1150
                                                             *
gccgccggag ctgtccgaca ccaccaacgc cacgcaaccc gaactcgttc
cggcggcctc gacaggctgt ggtggttgcg gtgcgttggg cttgagcaag
_____a_____GD-2 MRNA_a_____a_____>

1160        1170        1180        1190         1200
                                                             *
cggaagaccc cgaggactcg gccctcttag aggatcccgc cgggacggtg
gccttctggg gctcctgagc cgggagaatc tcctagggcg gccctgccac
_____a_____GD-2 MRNA_a_____a_____>

1210        1220        1230        1240         1250
                                                             *
tcttcgcaga tccccccaaa ctggcacatc ccgtcgatcc aggacgtcgc
agaagcgtct agggggttt gaccgtgtag ggcagctagg tcctgcagcg
_____a_____GD-2 MRNA_a_____a_____>

1260        1270        1280        1290         1300
                                                             *
gccgcaccac gcccccgccg ccccagcaa cccgggcctg atcatcggcg
cggcgtggtg cgggggcggc ggggtcgtt gggcccggac tagtagccgc
_____a_____GD-2 MRNA_a_____a_____>

1310        1320        1330        1340         1350
                                                             *
cgctggccgg cagtaccctg gcggcgctgg tcatcggcgg tattgcgttt
gcgaccggcc gtcatgggac cgccgcgacc agtagccgcc ataacgcaaa
_____a_____GD-2 MRNA_a_____a_____>
```

FIG. 2D

```
       1360       1370       1380       1390       1400
                                                       *
   tgggtacgcc gccgcgctca gatggccccc aagcgcctac gtctccccca
   acccatgcgg cggcgcgagt ctaccggggg ttcgcggatg cagaggggggt
   _____a_____GD-2 MRNA_a_____a_____>

1410       1420       1430       1440       1450
                                                       *
   catccgggat gacgacgcgc cccnctcgca ccagccattg ttttactaga
   gtaggccc ta ctgctgcgcg gggggagcgt ggtcggtaac aaaatgatct
   _____a_____GD-2 MRNA_a_____a_____>

1460       1470       1480       1490       1500
                                                       *
   ggagtttccc cgttcccgtg tacctctggg cccgtgtggg agggtggccg
   cctcaaaggg gcaagggcac atggagaccc gggcacaccc tcccaccggc 1510       1520       1530       1540       1550
                                                       *
   gggtatttgg gtgggacttg gactccgcat aaagggagtc tcgaaggagg
   cccataaacc caccctgaac ctgaggcgta tttccctcag agcttcctcc 1560       1570       1580       1590       1600
                                                       *
   gaaactagga cagttcatag gccgggagcg tggggcgcgc accgcgtccc
   ctttgatcct gtcaagtatc cggccctcgc accccgcgcg tggcgcaggg 1610       1620       1630
   gacgattagc caccgcgccc acagccacct cgacc
   ctgctaatcg gtggcgcggg tgtcggtgga gctgg
```

FIG. 2E

Ex. Removal of HSVgD TMR

*= cellular protease site

*= cleavage site for protease supplied in trans for ex. HIV protease

*= self cleaving protein such as the polio 3C protease or an intein

DNA VACCINES FOR HERPES SIMPLEX VIRUS

CROSS REFERENCE TO RELATED APPLICATIONS

This application claims the benefit of U.S. Provisional Application Ser. No. 60/028,754, filed Oct. 23, 1996 (now abandoned), and U.S. Provisional Application Ser. No. 60/053,206, filed Jul. 21, 1997 (now abandoned), which are both incorporated herein by reference.

FIELD OF THE INVENTION

The present invention relates to protective and therapeutic vaccines including vaccines for herpes simplex virus, to methods for preventing herpes simplex virus infection and treating individuals who have been infected with herpes simplex virus and to compositions for and methods of making prophylactic and therapeutic vaccines for herpes simplex virus.

BACKGROUND OF THE INVENTION

Herpes simplex virus (HSV), which includes both herpes simplex virus 1 (HSV1) and herpes simplex virus 2 (HSV2), presents a serious health concern to those infected by the virus as well as to uninfected members of the population. A great deal of effort has been expended to identify effective therapeutic compositions and methods to alleviate symptoms and reduce or eliminate viral flair-ups in which the dormant virus becomes active and presents itself as sores on the genital or oral tissues. In addition, vaccines are under development to prevent infection in uninfected individuals. One type of vaccine under development is a subunit vaccine containing purified glycoprotein D (gD). The gD protein may be derived from HSV-1 (gD-1) or HSV-2 (gD-2).

While such therapeutic compositions and vaccines may offer some benefits, there remains a need for effective compositions and methods of immunizing individuals prophylactically against HSV infection and methods of treating HSV infected individuals. There is a need for compositions and methods for making such prophylactics and therapeutics.

SUMMARY OF THE INVENTION

The present invention relates to isolated herpes simplex virus genes including HSV2 gD2 and to modified forms of that gene. The modified forms of HSV2 gD2 include those which lack a functional transmembrane region and/or a functional signal peptide.

The present invention relates to plasmids which comprise nucleotide sequences that encode either HSV2 gD2 or a modified version of HSV gD2 operably linked to regulatory elements necessary for expression in eukaryotic cells.

The present invention relates to a method of inducing, in an individual, an immune response against HSV2 gD2 comprising the step of administering to an individual, a plasmid which comprises a nucleotide sequence that encodes HSV2 gD2 or a modified form of HSV gD2 operably linked to regulatory elements necessary for expression in eukaryotic cells.

The present invention relates to a method of treating an individual who is infected with HSV comprising the step of administering to the individual, a plasmid which comprises a nucleotide sequence that encodes HSV2 gD2 or a modified form of HSV gD2 operably linked to regulatory elements necessary for expression in eukaryotic cells.

The present invention relates to a method of preventing an individual from becoming infected by HSV which comprises administering a nucleotide sequence that encodes HSV2 gD2 or a modified form of HSV gD2 operably linked to regulatory elements necessary for expression in eukaryotic cells.

The present invention relates to DNA vaccines which comprise nucleotide sequences that encode HSV2 gD2 or a modified form of HSV gD2 operably linked to regulatory elements necessary for expression in eukaryotic cells. In some embodiments, the vaccine comprises plasmids which include the nucleotide sequences that encode HSV2 gD2 or a modified from thereof. In some embodiments, the vaccines are facilitated DNA vaccines which further comprise a polynucleotide function enhancer or other facilitating composition.

BRIEF DESCRIPTION OF THE DRAWINGS

FIGS. 1A–1D show gD constructs.

FIGS. 2A–2E shows the sequence for HSV gD from Genbank (SEQ ID NO.1).

FIGS. 3A–3E show various inserts and plasmids having gD2 deletions in the HSV gD2 coding sequences.

FIGS. 4A–4E show humoral responses in immunized mice. AntigD2 specific serum antibodies in mice immunized with the indicated gD2 expression vectors were measured at day 79 by standard ELISA. Serum samples were diluted 1:100.

FIG. 5 shows antibody isotyping. The relative levels of IgG1 and IgG2A gD2-specific antibodies at day 79 were determined by standard ELISA.

FIGS. 6A–6E show lymphoproliferative responses of mouse spleen cells following immunization. $10^5$ whole spleen cells from mice immunized with 40 μg of DNA were cultured with 20 ng gD2/well. After 4 days of incubation, cells were incubated with 1 μCi $^3$H-thymidine for 18 hours. Lymphoproliferation was then measured as a function of $^3$H-thymidine uptake.

FIGS. 7A–7C shows constructs according to the invention.

DETAILED DESCRIPTION OF THE INVENTION

The present invention relates to improved DNA vaccines and vaccine protocols, and compositions and methods for making the same. The present invention relates to improved DNA anti-HSV vaccines and vaccine protocols, and compositions and methods for making the same. The present invention provides HSV2 gD2 cDNA which can be incorporated into vaccines. Additionally, the present invention provides coding sequences for modified HSV2 gD2 which can be incorporated into vaccines. In some embodiments, the modified HSV gD2 lacks a functional signal peptide. In some embodiments, the modified HSV gD2 lacks a functional transmembrane region (TMR). In some embodiments, the modified HSV gD2 lacks a functional signal peptide and a functional transmembrane region.

A wild type—or full length construct contains a signal peptide that directs the gD polypeptide into the endoplasmic reticulum where it is glycosylated. It travels to the cell surface through the secretory pathway and remains associated with the surface membrane via the transmembrane region (TMR), a hydrophobic region located near the C-terminus.

A TMR deletion construct was made in order to be secreted from cells and be available to be picked up by antigen presenting cells and boost the humoral response to gD. A cellular response may also be boosted. We have demonstrated that cells transferred with this construct secrete it into the media and that there is no detectable gD associated with the cell membrane.

Signal peptide deletion constructs were made to be localized to the cytoplasm and perhaps be misfolded. This provides a means by which more gD is transported to the proteosome, resulting in more gD derived peptide being able to complex with MHC Class 1 molecules. This boosts the cellular response to gD. There are two signal peptide deletion type constructs. One has a TMR and the other does not. Both types of proteins are expected to be localized to the cytoplasm but may have differences in distribution within the cytoplasm based on differences in their hydrophobicities.

We have demonstrated that cells transfected with these constructs express gD that is localized to the cytoplasm. There is no detectable gD associated with the cell membrane and no gD detected in the media of transfected cells. Based on the molecular weight of the expressed gD, it appears to be unglycosylated.

FIG. 1A shows a diagram of the HSV2 gD2 protein. In some embodiments, a nucleotide sequence that encodes this protein under the control of regulatory sequences is included in a vaccine. In some preferred embodiments, the vaccine is a DNA vaccine.

Figure 1B:

FIG. 1B shows a diagram of a HSV2 gD2 protein with a TMR deletion. In some embodiments, the entire TMR is deleted. In some embodiments, the TMR function is inhibited by deleting most of the TMR coding sequence. In some embodiments, a nucleotide sequence that encodes this protein under the control of regulatory sequences is included in a vaccine. In some preferred embodiments, the vaccine is a DNA vaccine.

Figure 1C:
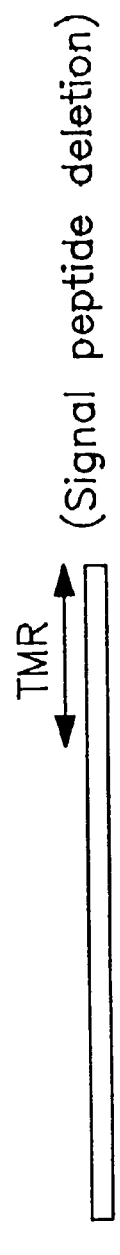

FIG. 1C shows a diagram of a HSV2 gD2 protein with a signal peptide deletion. In some embodiments, the entire signal peptide is deleted. In some embodiments, the signal peptide function is inhibited by deleting most of the signal peptide coding sequence. In some embodiments, a nucleotide sequence that encodes this protein under the control of regulatory sequences is included in a vaccine. In some preferred embodiments, the vaccine is a DNA vaccine.

Figure 1D:

FIG. 1D shows a diagram of a HSV2 gD2 protein with a TMR deletion and a signal peptide deletion. In some embodiments, the entire TMR is deleted. In some embodiments, the TMR function is inhibited by deleting most of the TMR coding sequence. In some embodiments, the entire signal peptide is deleted. In some embodiments, the signal peptide function is inhibited by deleting most of the signal peptide coding sequence. In some embodiments, a nucleotide sequence that encodes this protein under the control of regulatory sequences is included in a vaccine. In some preferred embodiments, the vaccine is a DNA vaccine.

The data in FIGS. 4A–4E, 5 and 6A–6E demonstrate that by removing the TMR of the HSV gD protein, a shift in IGg antibody isotype from IgG2a to IgG1 was obtained. This shift is considered a surrogate marker indicating a shift from a predominantly TH1 to a predominantly TH2 response, or from a cellular to an antibody response. Cytokines released by the cells would also be expected to differ accordingly.

A similar effect may be achieved by deleting or mutating the sequence coding for the TMR or membrane binding region of any protein normally anchored in the membrane. e.g., other herpes virus envelope proteins, HSV1, HSV2, EBV, CMV, HZV. This list of viruses is only a partial list and those having ordinary skill in the art can readily select other viruses which can be used to practice the invention. Further, other proteins which can be used include cell envelope associated protein. Likewise, proteins that enter the secretory pathway but contain other membrane retention signals such as endoplasmic retention signals from other viruses as well as host cellular proteins that are cell envelope associated could be made to secrete by removing or otherwise deleting the TMR or other membrane retention signal. In addition, proteins encoded by cells or viruses that are not envelope associated can be designed to be secreted by adding a signal peptide and removing membrane or cell compartment localization signals.

Secretion, with a resulting shift to a predominantly TH2 response, can be achieved where this is desired by the following changes to the construct:

1) removing or mutating the TMR or membrane binding region;
2) adding a signal or leader sequence;
3) co-expressing with a protease that clips the membrane binding region at an added protease site, or,
4) adding a sequence coding for an intein, which will self-cleave. The intein coding sequence would be inserted into the gene in a way that would result in a cleavage that would separate the TMR from the rest of the gene. In this way you would maintain the TMR protein expression which may contain an immunological epitope and yet render the TMR incapable anchoring the protein to the cell envelope.

If retention of the protein in the cell is desired, a signal or leader sequence can be removed, or if targeting specifically to the ER (endoplasmic reticulum) is desired, an ER retention signal and a sequence for a secretory peptide may be added.

The ability to shift the immune response from primarily Th1 to primarily Th2 allows for the design of improved vaccine protocols. In some embodiments, the primary and possibly first boost is designed to yield a Th1 response. The first boost or subsequent boosts may be designed to drive a Th2 response, thus affording the vaccinee improved protection.

In some preferred embodiments, the constructs described in FIGS. 1A–1D are incorporated into DNA vaccines. DNA vaccines are described in U.S. Pat. No. 5,589,466 and U.S. Pat. No. 5,593,971, which are incorporated herein by reference, PCT/US90/01515, PCT/US93/02338, PCT/US93/048131, PCT/US94/00899, and the priority applications cited therein, which are each incorporated herein by reference, and U.S. Ser. No. 08/642,045 filed May 6, 1996 which is incorporated herein by reference. In addition to the delivery protocols described in those applications, alternative methods of delivering DNA are described in U.S. Pat. Nos. 4,945,050 and 5,036,006, which are both incorporated herein by reference.

Using DNA vaccine technology, plasmid DNA that includes the coding sequences described in FIG. 1A–1D operably linked to regulatory elements required for gene expression is administered to individuals. The cells of the individual take up the plasmid DNA and the coding sequence is expressed. The antigen so produced becomes a target against which an immune response is directed. The immune response directed against the antigen provides the prophylactic or therapeutic benefit to the individual against HSV.

DNA vaccines include naked and facilitated vaccines. Further, they may be administered by a variety of techniques including several different devices for administering substances to tissue. The published literature includes several review articles that describe aspects of DNA vaccine technology and cite some of the many reports of results obtained using the technology. The following review articles which are each incorporated herein by reference as are each of the references cited in each review article discuss DNA vaccine technology: McDonnel W. M and F. K. Askari 1996 New Engl. J. Med. 334(1)42–45; Robinson, A. 1995 Can. Med. Assoc. J. 152(10):1629–1632; Fynan, E. F. et al. 1995 Int. J. Immunopharmac. 17(2)79–83; Pardoll, D. M. and A. M. Beckerleg 1995 Immunity 3:165–169; and Spooner et al. 1995 Gene Therapy 2:173–180.

According to the present invention, the coding sequence of the inserts described in FIG. 1A–1D are inserted into the plasmid which is then used in a vaccine composition.

As used herein, the term insert is meant to refer to a nucleotide sequence that encodes a gD2 protein described in FIG. 1A–1D including nucleotide sequences that encode a gD2 protein which comprises a non-functional TMR and/or a non-functional signal peptide.

As used herein, the term genetic construct is meant to refer to plasmids which comprise an insert operably linked to regulatory elements required for expression of the insert in eukaryotic cells. Regulatory elements for DNA expression include a promoter and a polyadenylation signal. In addition, other elements, such as a Kozak region, may also be included in the genetic construct. Initiation and termination signals are required regulatory elements which are often considered part of the coding sequence. The coding sequences of genetic constructs of the invention include functional initiation and termination signals.

The present invention relates to methods of introducing genetic material into the cells of an individual in order to induce immune responses against HSV. The methods comprise the steps of administering to the tissue of said individual, DNA that includes a coding sequence for an insert such as those shown in FIGS. 1A–1D operably linked to regulatory elements required for expression.

The present invention provides genetic constructs useful as DNA vaccines that include coding sequences for inserts such as those shown in FIGS. 1A–1D.

In some embodiments, the cDNA reported by Watson et al. 1983 Gene 26:307–312, which is incorporated herein by reference is used to construct inserts. The sequence is published in Genbank accession number K01408, which is incorporated herein by reference, and shown in FIG. 2. The coding sequence of the Watson clone spans nucleotides 268–1449. The sequence encoding the signal peptide includes nucleotides 268–342. The TMR is encoded by nucleotides 1249–1446.

In some embodiments, the insert comprises the entire coding sequence. In some embodiments, the insert consists of the entire coding sequence.

In some embodiments, the insert comprises the entire coding sequence which includes a frame shift or deletion or insertion that renders the signal peptide inoperable without effecting the remaining portions of the protein. In some embodiments, the sequence encoding the signal peptide is deleted and the insert comprises the remaining coding sequence. In some embodiments, less than the complete sequence that encodes the signal peptide is included, such as for example, inserts that include only nucleotides 287–1449, 297–1449, 307–1449, 317–1449, 327–1449 and 337–1449.

In some embodiments, the insert comprises the entire coding sequence which includes a frame shift or deletion or insertion that renders the TMR inoperable without effecting the remaining portions of the protein. In some embodiments, the sequence encoding the TMR is deleted and the insert comprises the remaining coding sequence. In some embodiments, less than the complete sequence that encodes the TMR is included, such as for example, inserts that include only nucleotides 268–1426, 268–1406, 268–1386, 268–1366, 268–1346, 268–1326, 268–1306, 268–1286, 268–1266 and 268–1246.

In some embodiments, the insert comprises the entire coding sequence which includes a frame shift or deletion or insertion that renders the signal peptide inoperable and a frame shift or deletion or insertion which renders the TMR inoperable without effecting the remaining portions of the protein. In some embodiments, the sequence encoding the signal peptide is deleted and the insert comprises the remaining coding sequence with a deleted or inoperable TMR. In some embodiments, the sequence encoding the TMR is deleted and the insert comprises the remaining coding sequence with a deleted or inoperable signal peptide. In some embodiments, the sequences encoding the signal peptide and TMR are deleted. In some embodiments, the insert consists of nucleotides 278–1426, 288–1386, 298–1346, 308–1306, 318–1266, 328–1246, and 342–1248.

In some embodiments, the insert is inserted into plasmid described in PCT/US94/00899 filed Jan. 26, 1994 and published as WO 94/16737 on Aug. 4, 1994, which is incorporated herein by reference. In some embodiments, the insert is inserted into plasmid described in U.S. Ser. No. 08/642,045 filed May 6, 1996, which is incorporated herein by reference.

According to the present invention, compositions and methods are provided which prophylactically and/or therapeutically immunize an individual against HSV, which includes HSV1 and HSV2, particularly HSV2. The genetic material, i.e. an insert, encodes a target protein, i.e. gD2 with or without a functioning signal peptide and/or TMR. The genetic material is expressed by the individual's cells and serves as an immunogenic target against which an immune response is elicited.

The present invention is useful to elicit immune responses against HSV2 gD2 protein. The immune response elicited may cross react with HSV1 gD1 protein. The present invention is useful to immunize individuals against HSV, particularly HSV2, such that an immune response against HSV2 gD2 provides protective immunity against HSV. The present invention is useful to combat HSV in infected individuals by eliciting an immune response against HSV gD2 which can be directed at infected cells that are expressing viral proteins.

According to the present invention, DNA encodes the unmodified or modified HSV2 gD2 protein operably linked to regulatory elements. Regulatory elements for DNA expression include a promoter and a polyadenylation signal. In addition, other elements, such as a Kozak region, may also be included in the genetic construct.

As used herein, the term "expressible form" refers to gene constructs which contain the necessary regulatory elements operably linked to the insert such that when present in the cell of the individual, the insert will be expressed.

When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal.

Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the immunogenic target protein. It is necessary that these elements be operably linked to the sequence that encodes the desired proteins and that the regulatory elements are operable in the individual to whom they are administered.

Initiation codons and stop codon are generally considered to be part of a nucleotide sequence that encodes the immunogenic target protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego, Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with a mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells into which the construct is administered. Moreover, codons may be selected which are most efficiently transcribed in the cell. One having ordinary skill in the art can produce DNA constructs which are functional in the cells.

The method of the present invention comprises the steps of administering nucleic acid molecules to tissue of the individual. In some preferred embodiments, the nucleic acid molecules are administered intramuscularly, intranasally, intraperatoneally, subcutaneously, intradermally, or topically or by lavage to mucosal tissue selected from the group consisting of vaginal, rectal, urethral, buccal and sublingual.

In some embodiments, the nucleic acid molecule is delivered to the cells in conjunction with administration of a facilitating agent. Facilitating agents are also referred to as polynucleotide function enhancers or genetic vaccine facilitator agents. Facilitating agents are described in U.S. Ser. No. 08/008,342 filed Jan. 26, 1993, U.S. Ser. No. 08/029,336 filed Mar. 11, 1993, U.S. Ser. No. 08/125,012 filed Sep. 21, 1993 now issued as U.S. Pat. No. 5,593,972, and International Application Ser. No. PCT/US94/00899 filed Jan. 26, 1994 published on Aug. 4, 1994 as International Publication No. WO94/16737, which are each incorporated herein by reference. In addition, facilitating agents are described in PCT application Ser. No. PCT/US95/04071 filed Mar. 30, 1995, published as International Publication No. WO95/26718 on Oct. 12, 1995, which is incorporated herein by reference. Facilitating agents which are administered in conjunction with nucleic acid molecules may be administered as a mixture with the nucleic acid molecule or administered separately simultaneously, before or after administration of nucleic acid molecules. In addition, other agents which may function as transfecting agents and/or replicating agents and/or inflammatory agents and which may be co-administered with or without a facilitating agent include growth factors, cytokines and lymphokines such as -interferon, gamma-interferon, platelet derived growth factor (PDGF), GC-SF, GM-CSF, TNF, epidermal growth factor (EGF), IL-1, IL-2, IL-4, IL-6, IL-8, IL-10 and B7.2 as well as fibroblast growth factor, surface active agents such as immune-stimulating complexes (ISCOMS), Freund's incomplete adjuvant, LPS analog including monophosphoryl Lipid A (MPL), muramyl peptides, quinone analogs and vesicles such as squalene, and squalene, and hyaluronic acid may also be administered in conjunction with the genetic construct.

In some preferred embodiments, the genetic constructs of the invention are formulated with or administered in conjunction with a facilitator selected from the group consisting of benzoic acid esters, anilides, amidines, urethans and the hydrochloride salts thereof such as those of the family of local anesthetics.

The facilitator in some preferred embodiments may be a compound having one of the following formulae:

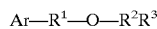

or

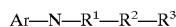

or

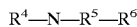

or

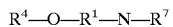

wherein:

Ar is benzene, p-aminobenzene, m-aminobenzene, o-aminobenzene, substituted benzene, substituted p-aminobenzene, substituted m-aminobenzene, substituted o-aminobenzene, wherein the amino group in the aminobenzene compounds can be amino, $C_1$–$C_5$ alkylamine, $C_1$–$C_5$, $C^1$–$C_5$ dialkylamine and substitutions in substituted compounds are halogen, $C_1$–$C_5$ alkyl and $C_1$–$C_5$ alkoxy;

$R^1$ is C=O;

$R^2$ is $C_1$–$C_{10}$ alkyl including branched alkyls;

$R^3$ is hydrogen, amine, $C_1$–$C_5$ alkylamine, $C_1$–$C_5$, $C_1$–$C_5$ dialkylamine;

$R^2$+$R^3$ can form a cyclic alkyl, a $C_1$–$C_{10}$ alkyl substituted cyclic alkyl, a cyclic aliphatic amine, a $C_1$–$C_{10}$ alkyl substituted cyclic aliphatic amine, a heterocycle, a $C_1$–$C_{10}$ alkyl substituted heterocycle including a $C_1$–$C_{10}$ alkyl N-substituted heterocycle;

$R^4$ is Ar, $R^2$ or $C_1$–$C_5$ alkoxy, a cyclic alkyl, a $C_1$–$C_{10}$ alkyl substituted cyclic alkyl, a cyclic aliphatic amine, a $C_1$–$C_{10}$ alkyl substituted cyclic aliphatic amine, a heterocycle, a $C_1$–$C_{10}$ alkyl substituted heterocycle and a $C_1$–$C_{10}$ alkoxy substituted heterocycle including a $C_1$–$C_{10}$ alkyl N-substituted heterocycle;

$R^5$ is C=NH;

$R^6$ is Ar, $R^2$ or $C_1$–$C_5$ alkoxy, a cyclic alkyl, a $C_1$–$C_{10}$ alkyl substituted cyclic alkyl, a cyclic aliphatic amine, a $C_1$–$C_{10}$ alkyl substituted cyclic aliphatic amine, a heterocycle, a $C_1$–$C_{10}$ alkyl substituted heterocycle and a $C_1$–$C_{10}$ alkoxy substituted heterocycle including a $C_1$–$C_{10}$ alkyl N-substituted heterocycle; and.

$R^7$ is Ar, $R^2$ or $C_1$–$C_5$ alkoxy, a cyclic alkyl, a $C_1$–$C_{10}$ alkyl substituted cyclic alkyl, a cyclic aliphatic amine, a $C_1$–$C_{10}$ alkyl substituted cyclic aliphatic amine, a heterocycle, a $C_1$–$C_{10}$ alkyl substituted heterocycle and a $C_1$–$C_{10}$ alkoxy substituted heterocycle including a $C_1$–$C_{10}$ alkyl N-substituted heterocycle.

Examples of esters include: benzoic acid esters such as piperocaine, meprylcaine and isobucaine; para-aminobenzoic acid esters such as procaine, tetracaine, butethamine, propoxycaine and chloroprocaine; meta-aminobenzoic acid esters including metabuthamine and primacaine; and para-ethoxybenzoic acid esters such as parethoxycaine. Examples of anilides include lidocaine, etidocaine, mepivacaine, bupivacaine, pyrrocaine and prilocaine. Other examples of such compounds include dibucaine, benzocaine, dyclonine, pramoxine, proparacaine, butacaine, benoxinate, carbocaine, methyl bupivacaine, butasin picrate, phenacaine, diothan, luccaine, intracaine, nupercaine, metabutoxycaine, piridocaine, biphenamine and the botanically-derived bicyclics such as cocaine, cinnamoylcocaine, truxilline and cocaethylene and all such compounds complexed with hydrochloride.

In preferred embodiments, the facilitator is bupivacaine. The difference between bupivacaine and mepivacaine is that bupivacaine has a N-butyl group in place of an N-methyl group of mepivacaine. Compounds may have at that N, $C_1$–$C_{10}$. Compounds may be substituted by halogen such as procaine and chloroprocaine. The anilides are preferred.

The facilitating agent is administered prior to, simultaneously with or subsequent to the genetic construct. The facilitating agent and the genetic construct may be formulated in the same composition.

Bupivacaine-HCl is chemically designated as 2-piperidinecarboxamide, 1-butyl-N-(2,6-dimethylphenyl)-monohydrochloride, monohydrate and is widely available commercially for pharmaceutical uses from many sources including from Astra Pharmaceutical Products Inc. (Westboro, Mass.) and Sanofi Winthrop Pharmaceuticals (New York, N.Y.), Eastman Kodak (Rochester, N.Y.). Bupivacaine is commercially formulated with and without methylparaben and with or without epinephrine. Any such formulation may be used. It is commercially available for pharmaceutical use in concentrations of 0.25%, 0.5% and 0.75% which may be used on the invention. Alternative concentrations, particularly those between 0.05%–1.0% which elicit desirable effects may be prepared if desired. According to the present invention, about 250 μg to about 10 mg of bupivacaine is administered. In some embodiments, about 250 μg to about 7.5 mg is administered. In some embodiments, about 0.05 mg to about 5.0 mg is administered. In some embodiments, about 0.5 mg to about 3.0 mg is administered. In some embodiments about 5 to 50 μg is administered. For example, in some embodiments about 50 μl to about 2 ml, preferably 50 μl to about 1500 μl and more preferably about 1 ml of 0.25–0.50% bupivacaine-HCl and 0.1% methylparaben in an isotonic pharmaceutical carrier are administered at the same site as the vaccine before, simultaneously with or after the vaccine is administered. Similarly, in some embodiments, about 50 μl to about 2 ml, preferably 50 μl to about 1500 μl and more preferably about 1 ml of 0.25–0.50% bupivacaine-HCl in an isotonic pharmaceutical carrier is administered at the same site as the vaccine before, simultaneously with or after the vaccine is administered. Bupivacaine and any other similarly acting compounds, particularly those of the related family of local anesthetics may be administered at concentrations which provide the desired facilitation of uptake of genetic constructs by cells.

In some embodiments of the invention, the individual is first subject to injection of the facilitator prior to administration of the genetic construct. For example, up to a about a week to ten days prior to administration of the genetic construct, the individual is first injected with the facilitator. In some embodiments, the individual is injected with facilitator about 1 to 5 days, in some embodiments 24 hours, before or after administration of the genetic construct. Alternatively, if used at all, the facilitator is administered simultaneously, minutes before or after administration of the genetic construct. Accordingly, the facilitator and the genetic construct may be combined to form a single pharmaceutical composition.

In some embodiments, the genetic constructs are administered free of facilitating agents, that is in formulations free from facilitating agents using administration protocols in which the genetic constructs are not administered in conjunction with the administration of facilitating agents.

The Herpes simplex 2 glycoprotein D (gD) gene encodes a glycoprotein that is associated with the viral envelope and the infected cell plasma membrane. A gD encoded signal peptide directs the translocation of the nascent polypeptide into the lumen of the endoplasmic reticulum where it enters the secretory pathway, is glycosylated and folded. The protein remains associated with the plasma membrane via a hydrophobic C-terminal domain referred to as the transmembrane region or TMR.

DNA immunization with a plasmid expressing Herpes simplex 2 glycoprotein D gene has been shown to induce humoral and cellular immune responses in several animal models. In mice, the immune response generated by the initial gD-expressing plasmid was found to be predominantly a TH1 or cellular response. We have demonstrated that a TH2 or humoral response may be induced during immunization if the gene is modified so that a predominantly secreted version of gD is expressed by the plasmid component of the vaccine. The encoded protein differs from the native gD 2 protein only in the deletion of the last 66 amino acids which encode the TMR. We have demonstrated that a construct engineered to encode a TMR-deleted protein expresses a protein which is predominantly secreted into the media of transfected cells. Only a small amount of protein remains cell-associated. High levels of soluble antigen have been shown to stimulate Th2 responses, while low doses of soluble antigen stimulate the production of IL-12, leading to Th1 responses (Abbas, A. K., Murphy, K. M., Sher, A. (1996). Functional diversity of helper T lymphocytes. Nature 381:787–793). A construct designed to favor secretion of antigen would promote Th2 immune responses.

Accordingly, the invention relates to engineered polynucleotide constructs capable of expressing an antigenic protein which will induce a desired TH1 or TH2 immune response, to plasmid or other vector constructs containing and capable of expressing such engineered polynucleotide constructs, and to methods of immunizing a mammal with such constructs in order to achieve a desired TH1 or TH2 immune response. In one desired embodiment, the invention relates to a method of engineering a gene or a group of genes so that the encoded protein(s) is secreted from the cell, thus enabling a TH2 response. In another desired embodiment, the invention relates to a method of immunizing wherein a mammal is first immunized at least once with a plasmid that encodes a protein that induces a TH1 response and subsequent immunizations are with a plasmid system that allows for the efficient secretion of that protein such that the response may be subsequently pushed towards a TH2 response. In some applications, the invention relates to a method wherein the mammal is first immunized with a polynucleotide vaccine that induces a TH2 response and then boosted with a vaccine that pushes a TH1 response. In another embodiment of the invention, both TH1 and Th2 responses may be achieved via simultaneous or contemporaneous immunization with one or more vaccine composition(s) that push(es) both a TH1 response and a TH2 response.

The constructs of the invention may engineered as follows:

In one preferred embodiment, a modified construct contains a TMR deletion which results in enhanced secretion of the expressed antigenic protein into the extracellular compartment, thereby producing an enhanced TH2 or humoral immune response. In one preferred embodiment, a modified construct contains a signal or leader peptide deletion which results in intracellular localization to the cytosol compartment, thereby resulting in an enhanced TH1 or cellular immune response. In another preferred embodiment, both signal and TMR deletions are made, resulting in the expression of an immunogenic protein which localizes to the cytosolic compartment, thereby resulting in an enhanced TH1 or cellular immune response.

The following describes a list of ways to enable secretion of cell associated proteins. It is first necessary to engineer a signal peptide at the amino terminus of a protein for cell associated proteins that do not enter the secretory pathway. This may be all that is needed for the efficient secretion of some of these proteins but other of these proteins will need further modification(s). For example, some proteins that are normally not secreted may contain domains that interact with membranes and this interaction may inhibit secretion of those proteins. Alternatively, these proteins may contain motifs that localize the protein to certain sub-cellular compartments such as the nucleus and it is possible that these sequences may also prevent efficient secretion of the protein. It would therefore be necessary to destroy these domains by deletion or mutation. In many instances these sequences will already be known, in other cases, homology to known domains and localization motifs can be identified by scanning the sequence. In other cases, unidentified inhibitory sequences can be mapped and destroyed via a selection based mutagenesis approach.

For proteins that normally enter the secretory pathway, but remain associated with the cell via membrane retention domains or domains that localize the protein to a sub-compartment within the secretory pathway, it will first be necessary to remove those domains. These can be removed via deletion or mutation. In some instances, the natural signal peptides encoded by these proteins may be inefficient at translocating the protein into the ER. In these cases, a heterologous signal peptide can be used in place of the native signal peptide. An example of a heterologous signal peptide would be the one encoded by the HSV2 gD gene.

Figure 7A:
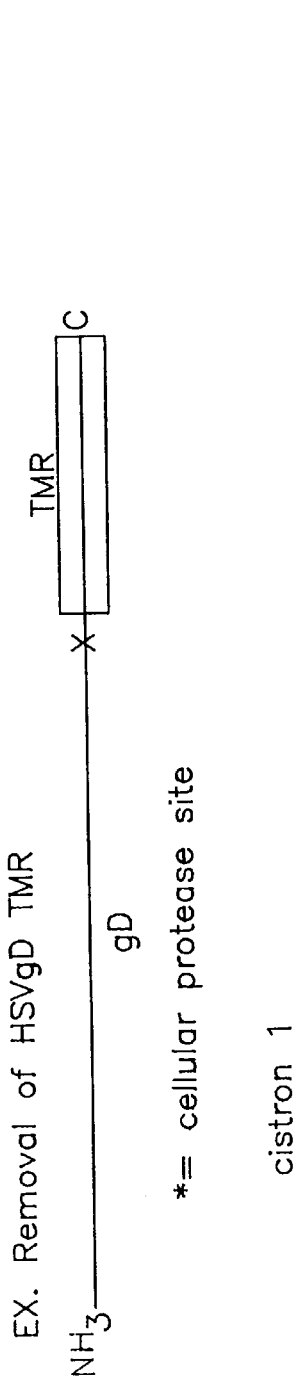
Figure 7B:
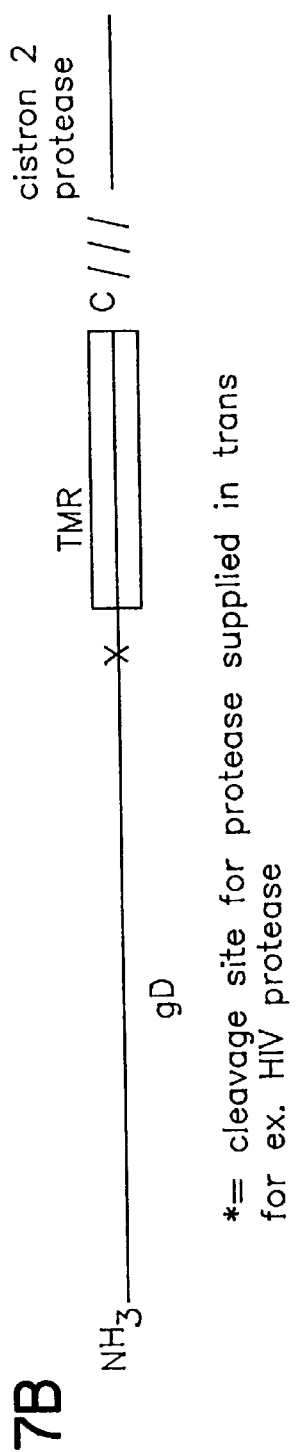
Figure 7C:
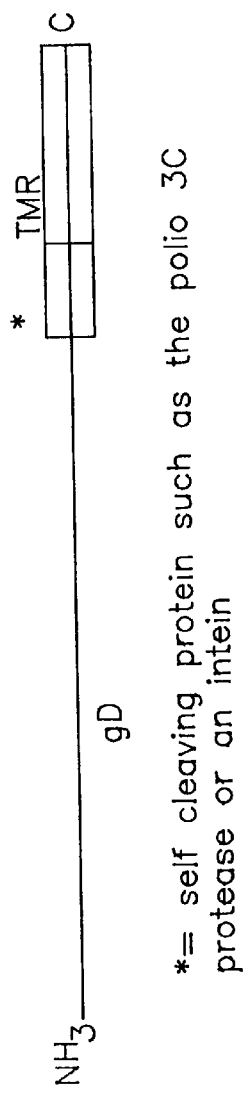

Deletion of sequences can be through deletion or mutation of the sequences in the construct itself (FIG. 7). Alternatively, in some cases where the inhibitory sequences exist as distinct domains (i.e, they are not marbled throughout the protein) and they are localized to the C-terminal end of the protein, and it is desirable to retain these sequences in the construct for immunogenicity purposes, the construct can be engineered in such a way that these sequences are not covalently joined to the portion of the protein destined for secretion. This can be done by encoding a protease site between the part of the protein to be secreted and the part of the protein with sequences inhibitory for secretion. This protease site would be a cleavage site for a protease that is endogenous to the cells expressing the vaccine protein. Alternatively, the protease could be provided in trans on either the same construct as the encoded vaccine protein or on a separate plasmid that would be co-injected with the vaccine plasmid. In this instance, cleavage would not be dependent on a protease that naturally occurs within cells that express the vaccine plasmid. It is also feasible to include a self-cleaving protease such as the polio 3C protease or an intein between the domains of the protein to be separated. There are some instances where it would not be feasible to remove domains by a protease approach. For example, a sub-cellular localization domain is first expressed as a part of a precursor polypeptide (prior to proteolysis) and could in effect interfere with nascent polypeptide translocation into the ER. In this instance, the domain would have to be removed through deletion or site-directed mutation. Also, one would have to ascertain if the desired proteolysis reaction will occur in the ER.

Another consideration for targeted secretion is the stability of the protein in the extracellular compartment. If the protein is unstable, it may be possible to increase its stability and maintain its antigenicity by fusing it to another peptide or protein such as a fusion protein. In some instances, the fusion proteins may be able to assemble into serum stable particles.

The invention also relates to polynucleotide constructs engineered to express fusion proteins which assemble to form particles, as well as methods of immunization with such polynucleotide constructs. Not only are such proteins stable, but they are of the size which is preferentially taken up by APCs (antigen presenting cells) and are processed in such a way that they are presented by both MHC class 1 and class 2 molecules.

Constructs of the invention modified to encode proteins that are predominantly secreted would be appropriate for a number of antigens for which a TH2 or humoral response would be required, as in a prophylactic vaccine against viral, parasitic and bacterial infections. The proteins that are chosen to be expressed would be those antigenic proteins that make up the viral particles, parasite, bacteria or spore. However, proteins that are not a part of the infecting organism per se, but are associated particularly with the infected cell membrane might also be targets for expression since a humoral response against these antigens could result in cell death via the complement pathway or ADCC pathway.

EXAMPLES

Example 1

Insert TMR consists of 37 nucleotides of HSV2 gD2 5' flanking sequence and sequences encoding the HSV gD2 leader peptide and the first 302 amino acids of the mature protein. 66 amino acids are deleted from the carboxy terminus. The construct has 1 nucleotide of the 3' HSV gD2 flanking sequence.

Figure 3A:
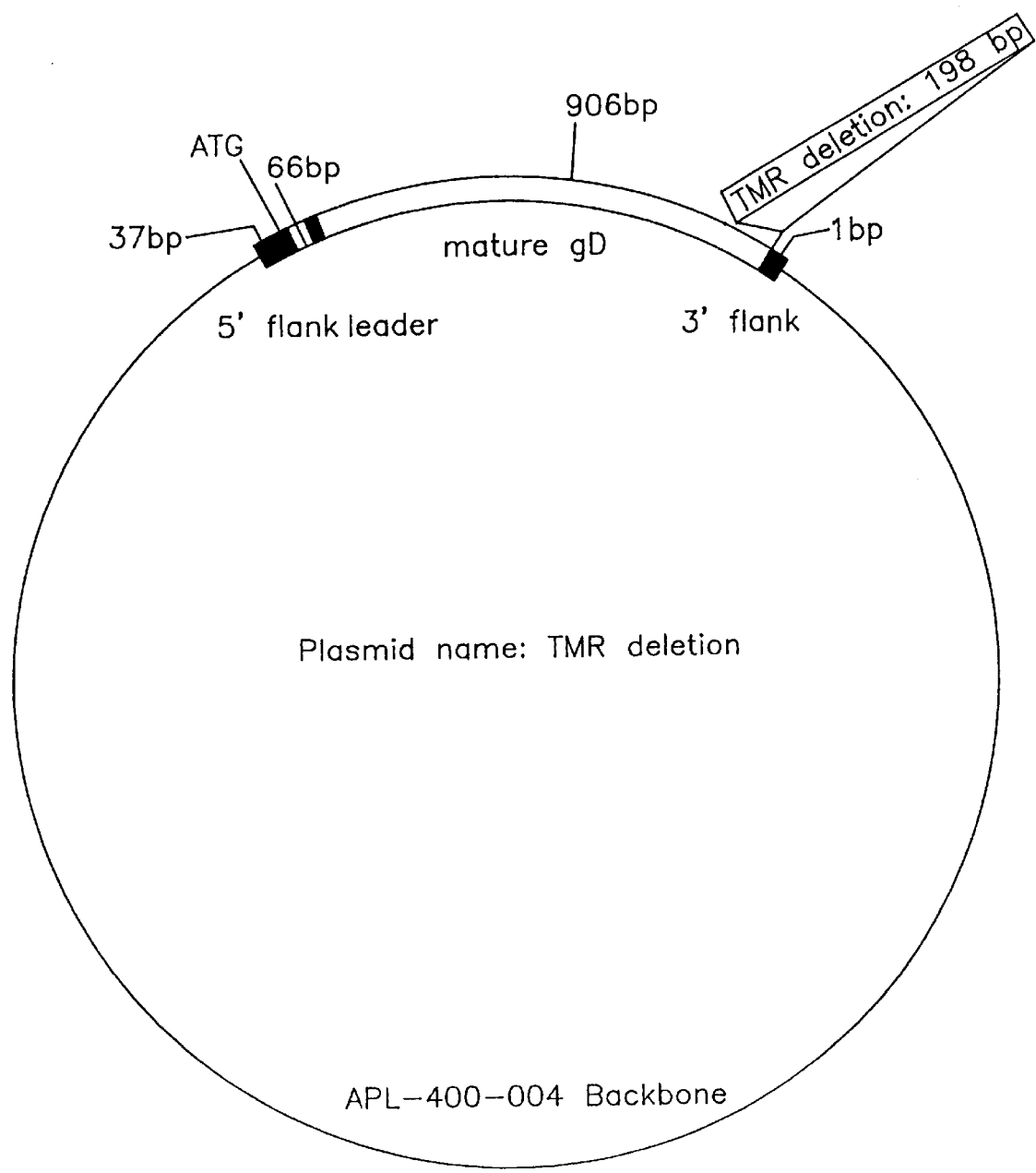

The insert is cloned into vector APL-400-004 to produce APL-400-004 TMR shown in FIG. 3A.

In some embodiments, a second construct, APL-400-024 TMR is prepared. That plasmid is identical to APL-400-004 TMR except the chimeric kanamycin resistance construct of U.S. Ser. No. 08/642,045 filed May 6, 1996 is inserted in place of the kanamycin resistance gene in the vector APL-400-004.

Example 2

Insert $L_{-1}$ consists of 9 bp of authentic 5' sequence flanking the ATG of HSV2 gD2 followed by the ATG and then the coding sequence for the mature protein coding region starting with amino acid 26. The coding sequence for the first 25 amino acids which comprise the leader peptide has been deleted. The insert also includes approximately 550 bp of 3' sequences flanking the stop codon.

Figure 3B:
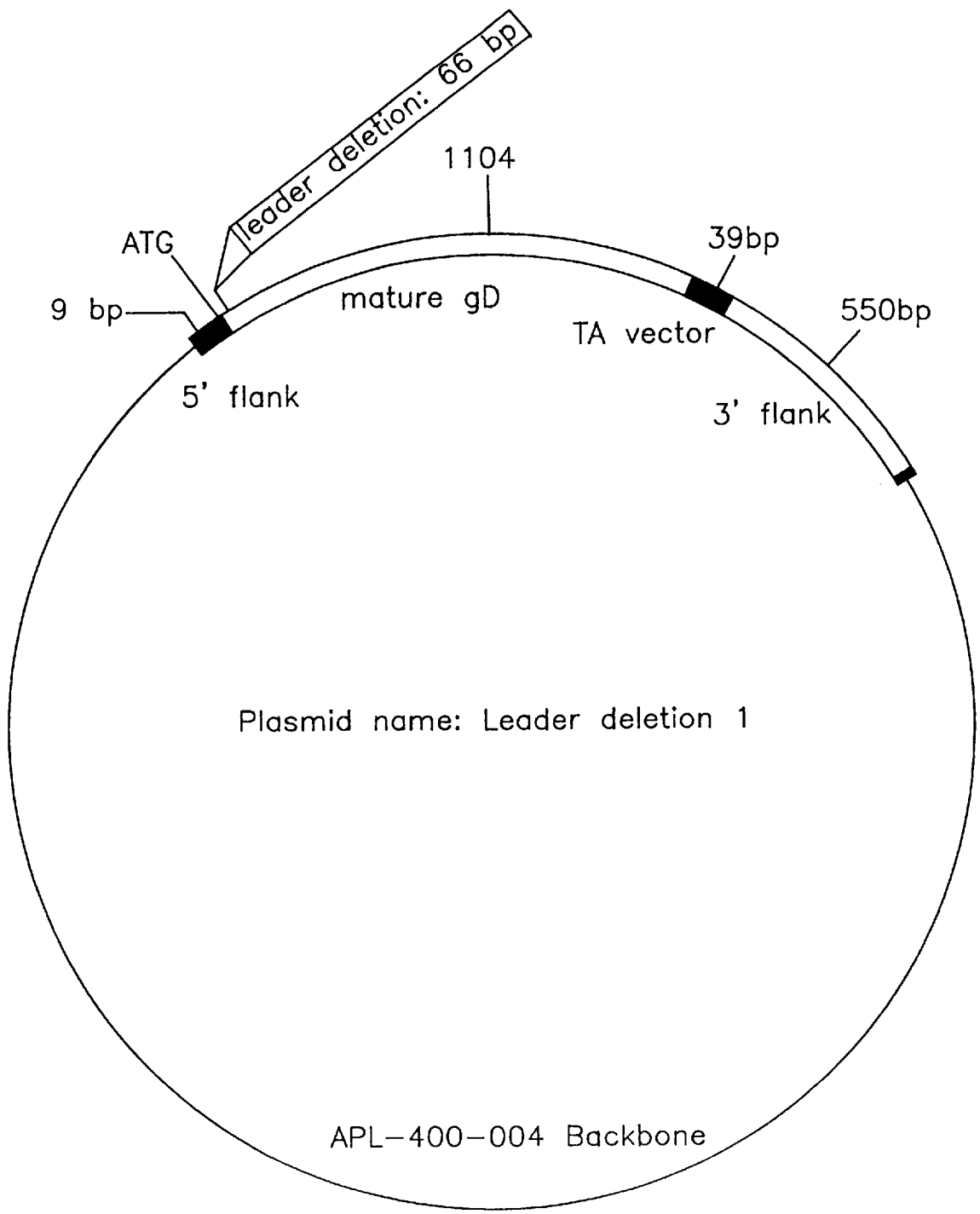

The insert is cloned into vector APL-400-004 to produce APL-400-004 $L_{-1}$ shown in FIG. 3B and further comprises 39 bp 5' of the authentic flanking (5') sequences is from the TA vector (PCR II, Invitrogen).

In some embodiments, a second construct, APL-400-024 $L_{-1}$ is prepared. That plasmid is identical to APL-400-004 $L_{-1}$ except it contains the chimeric kanamycin resistance construct of U.S. Ser. No. 08/642,045 filed May 6, 1996 in place of the kanamycin resistance gene in the vector APL-400-004.

Example 3

Insert $L_{-II}$, consists of 41 bp of authentic 5' sequences flanking the ATG of HSV2 gD2 followed by ATG and then the coding sequences for the mature protein coding region starting with amino acid 26. The coding sequence for the first 25 amino acids which comprise the leader peptide have been deleted. The insert also includes approximately 550 bp of 3' sequences following the stop codon.

Figure 3C:
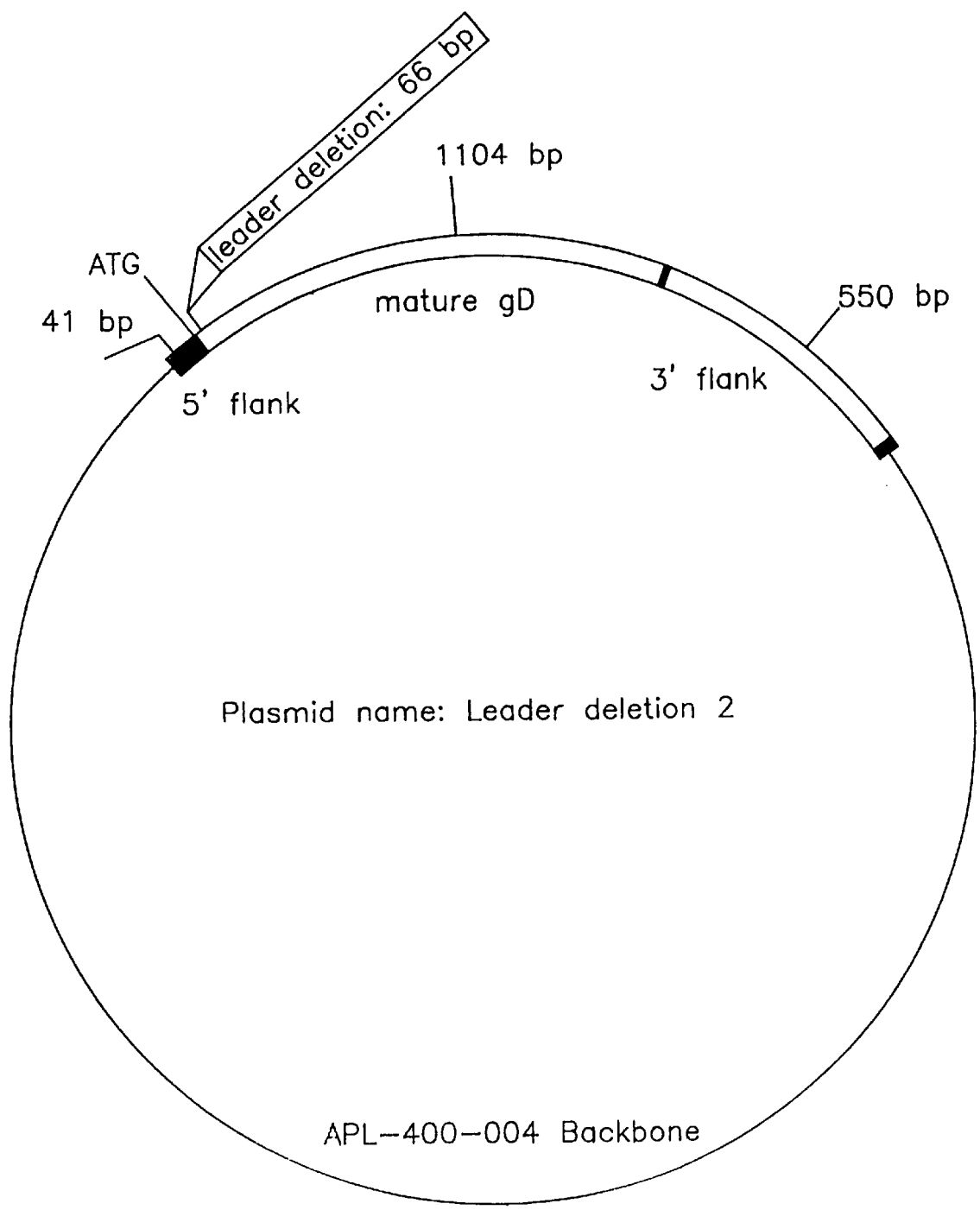

The insert is cloned into vector APL-400-004 to produce APL-400-004 $L_{-II}$ shown in FIG. 3C.

In some embodiments, a second construct, APL-400-024 $L_{-II}$ is prepared. That plasmid is identical to APL-400-004 $L_{-II}$ except having the chimeric kanamycin resistance construct of U.S. Ser. No. 08/642,045 filed May 6, 1996 in place of the kanamycin resistance gene in the vector APL-400-004.

Example 4

Insert $L_{-3}$ consists of 41 bp of authentic 5' sequences flanking the ATG of HSV2 gD2 followed by ATG and 6 bp after the ATG in order to preserve the Kozak site, and then the coding sequences for the mature protein coding region starting with amino acid 26. The coding sequence for the first 25 amino acids which comprise the leader peptide has been deleted. The insert also includes approximately 550 bp of 3' sequences following the stop codon.

Figure 3D:
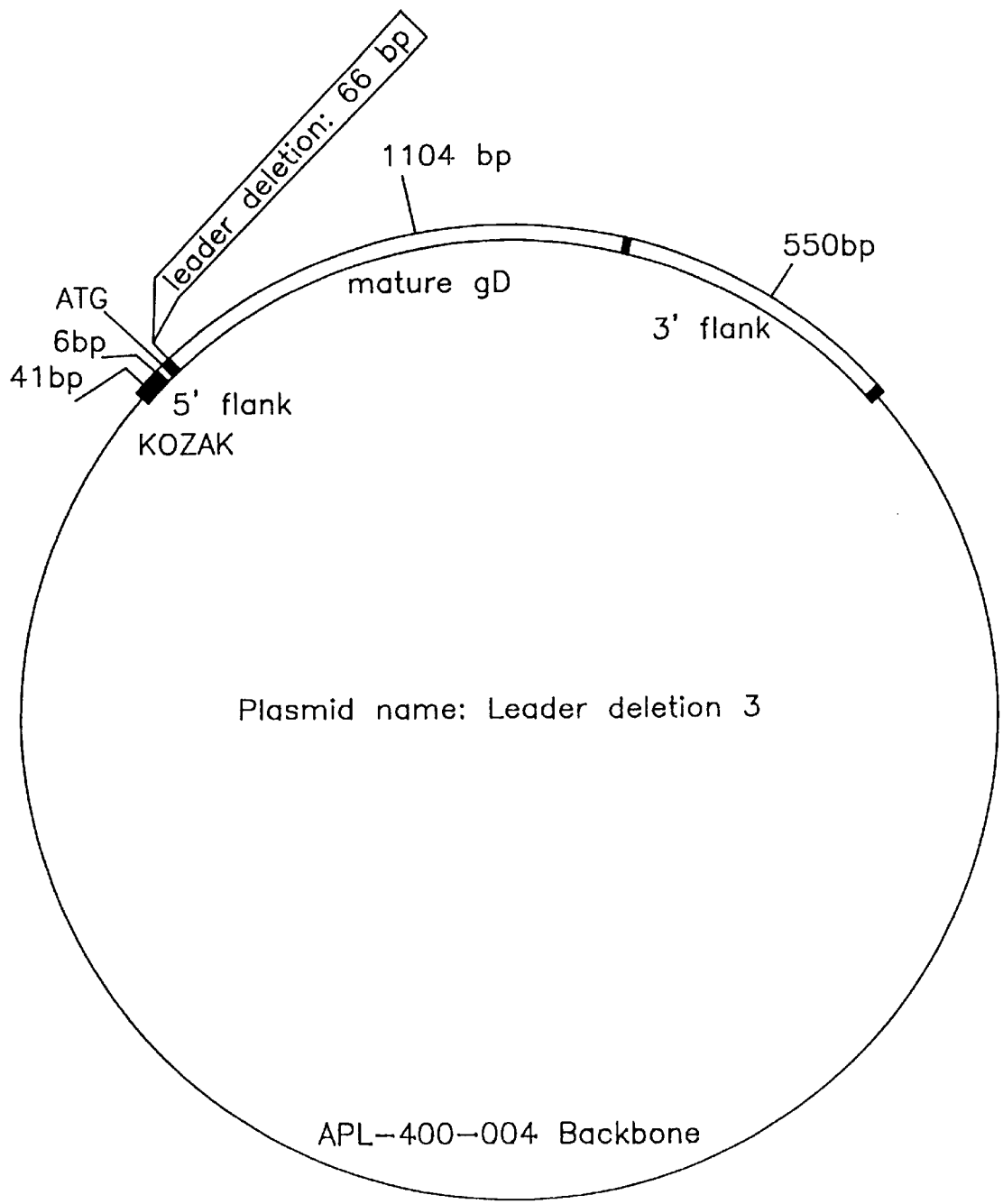

The insert is cloned into vector APL-400-004 to produce APL-400-004 $L_{-3}$ shown in FIG. 3D.

In some embodiments, a second construct, APL-400-024 $L_{-3}$ is prepared. That plasmid is identical to APL-400-004 $L0_{-3}$ except it the chimeric kanamycin resistance construct of U.S. Ser. No. 08/642,045 filed May 6, 1996 in place of the kanamycin resistance gene in the vector APL-400-004.

Example 5

Insert $L_{-3}$TMR consists of 41 bp of authentic 5' sequences flanking the ATG of HSV2 gD2 followed by ATG and 6 bp after the ATG in order to preserve the Kozak site, and then the coding sequences for the mature protein coding region starting with amino acid 26. The coding sequence for the first 25 amino acids which comprise the leader peptide and the coding sequence for the 66 amino acids at the carboxy terminus of the mature protein which comprise the transmembrane region have been deleted. The insert also includes 1 bp of 3' sequences following the stop codon.

Figure 3E:
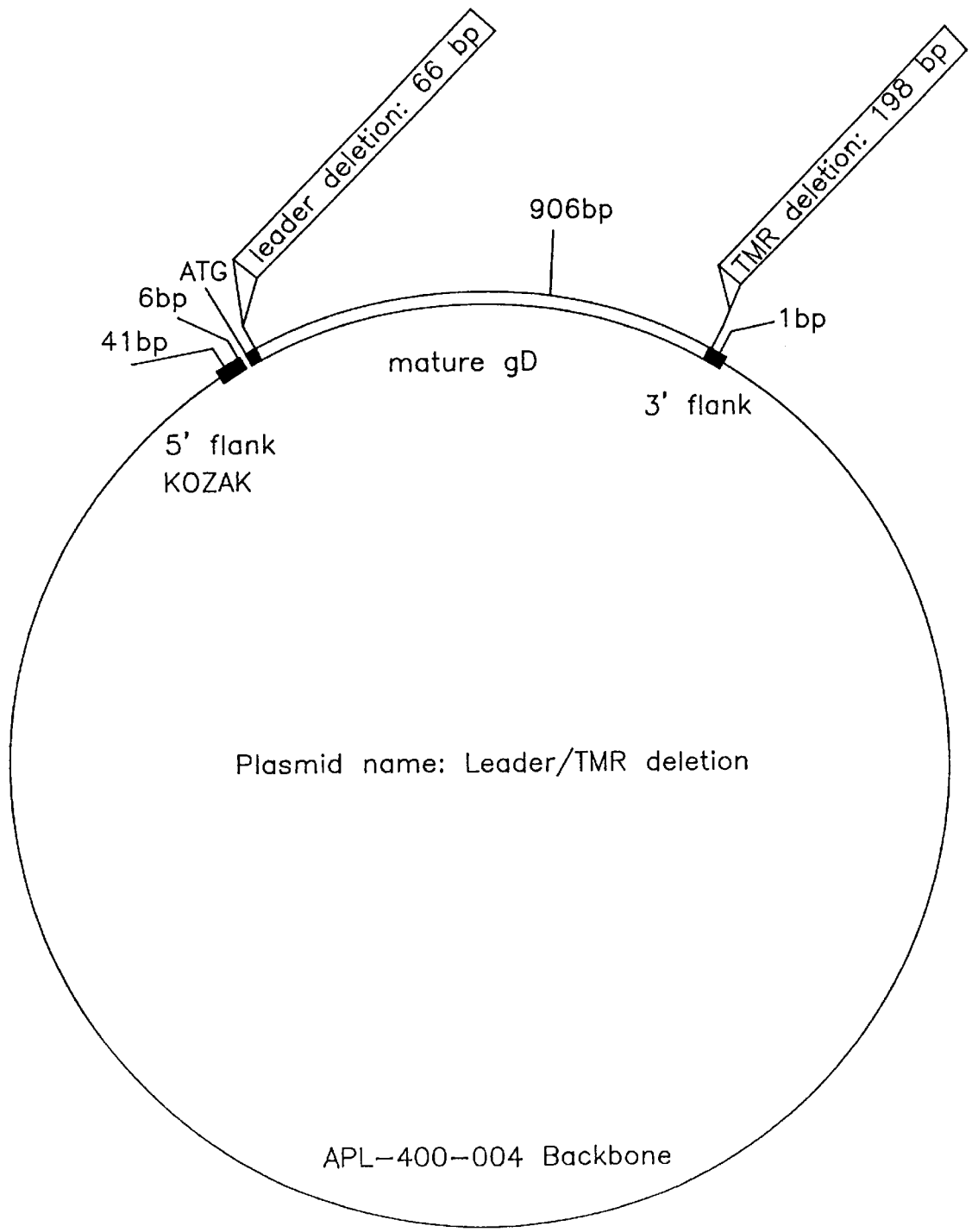
Figure 4A:
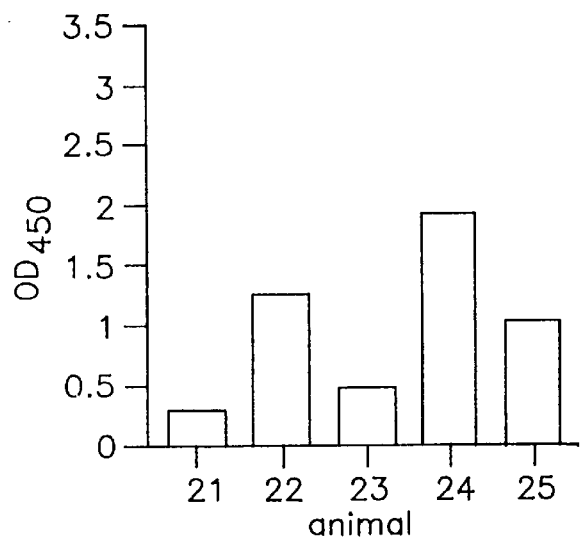
Figure 4B:
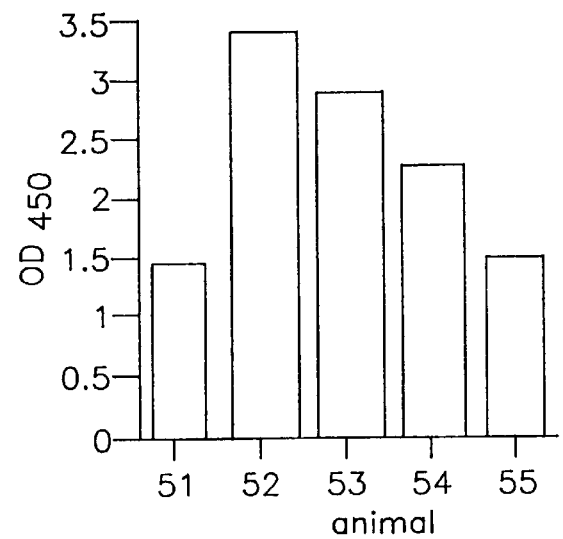
Figure 4C:
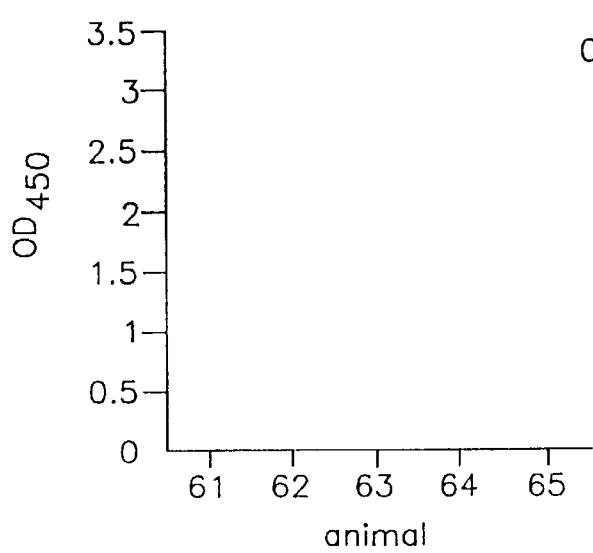
Figure 4D:
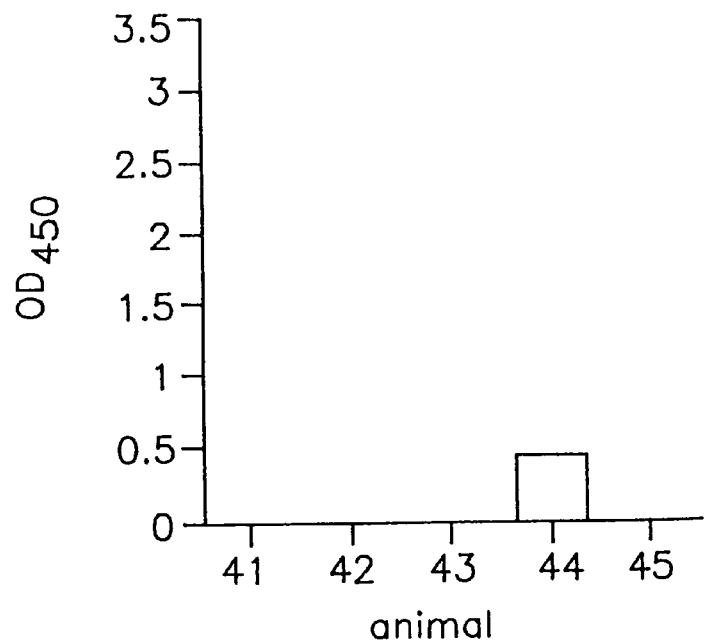
Figure 4E:
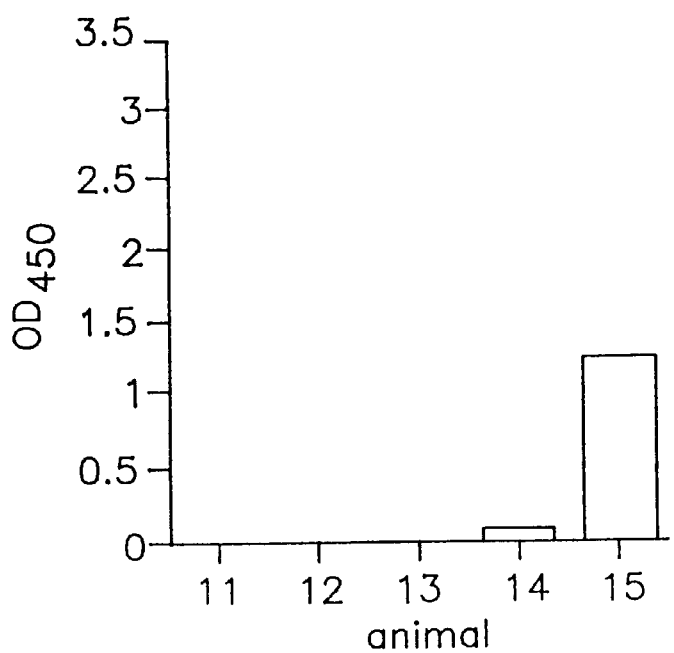
Figure 5:
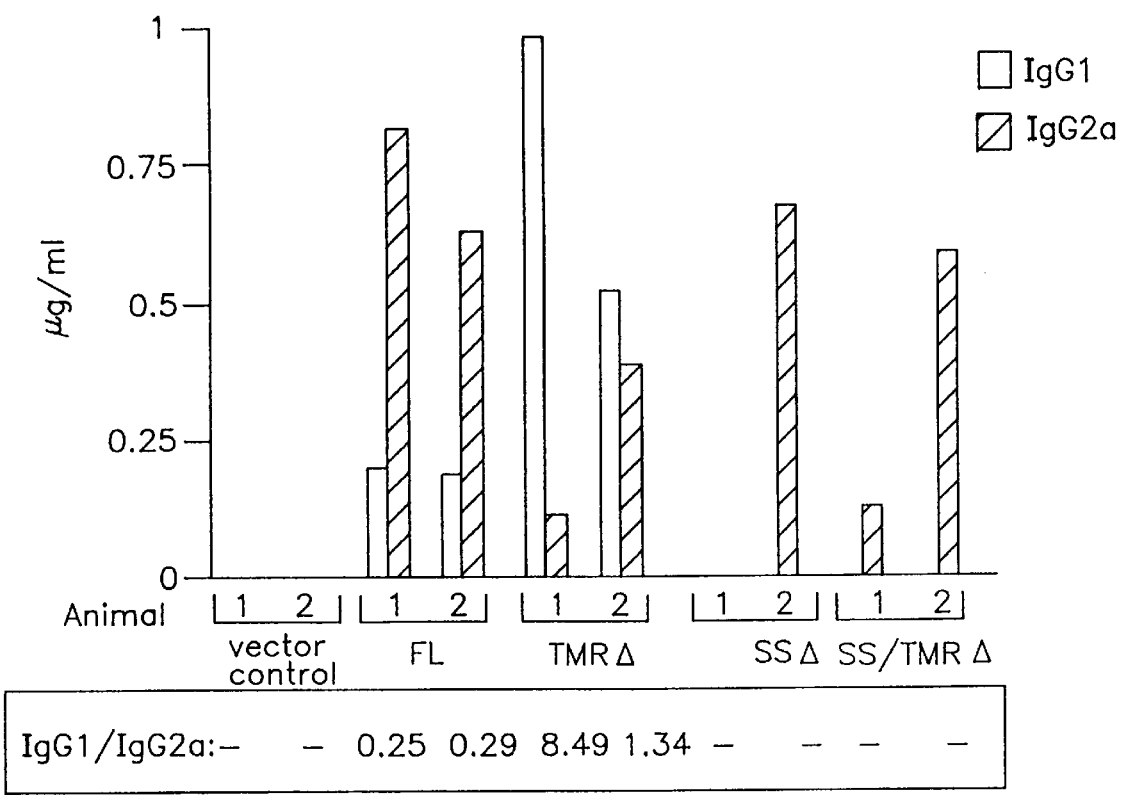
Figure 6A:
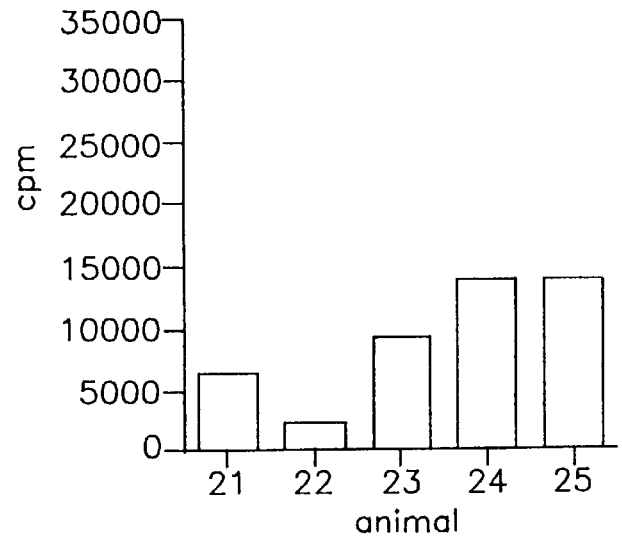
Figure 6B:
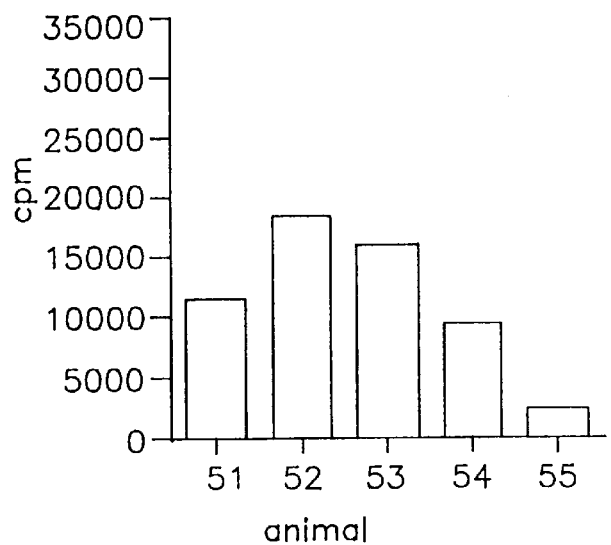
Figure 6C:
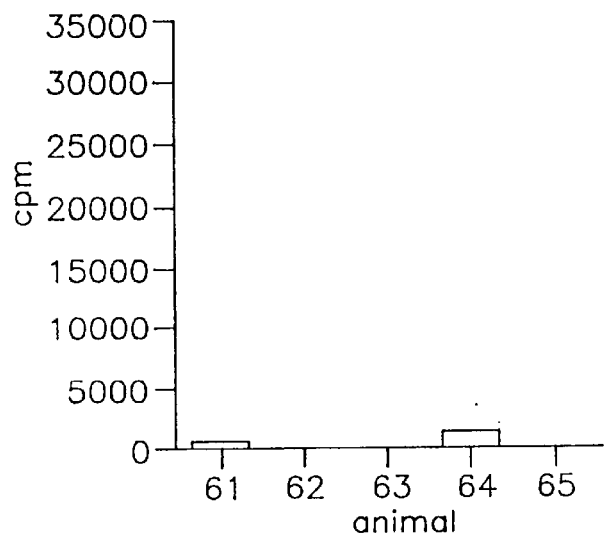
Figure 6D:
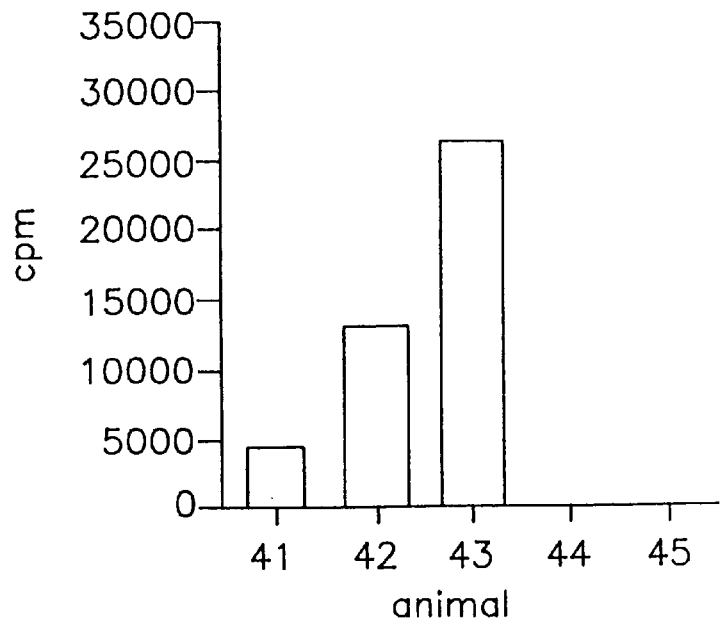
Figure 6E:
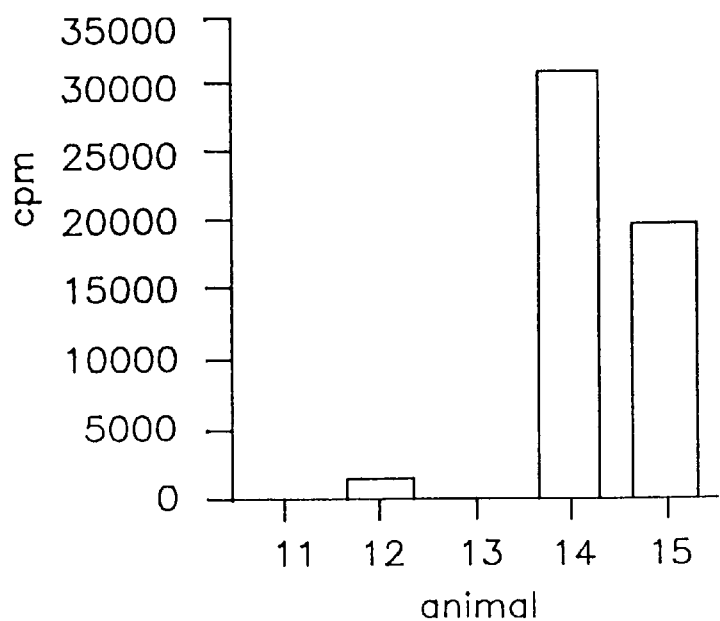

The insert is cloned into vector APL-400-004 to produce APL-400-004 $L_{-3}$ TMR shown in FIG. 3E.

In some embodiments, a second construct, APL-400-024 $L_{-3}$ TMR is prepared. That plasmid is identical to APL-400-004 $L_{-3}$ TMR except has the chimeric kanamycin resistance construct of U.S. Ser. No. 08/642,045 filed May 6, 1996 in place of the kanamycin resistance gene in the vector APL-400-004.

Example 6

Mice were immunized I.M. at day 0 and day 14 with 20 μg DNA/0.4% bupivacaine. Mice were bled at day 14 and day 42 and sera assayed for the presence of anti-gD antibodies. Mice immunized with the TMR deletion appeared to have mounted a higher humoral response than did mice immunized with the full length HSVgD construct. No seroconversion was detected in mice immunized with either of the signal peptide deletions.

We claim:

1. A method of inducing an increased MHC class I immune response in a mammalian subject by a Herpes Simplex Virus (HSV) glycoprotein D (gD) antigen, the method comprising the step of
    delivering to a mammalian cell an effective amount of a modified gene encoding an HSV gD antigen lacking a functional native signal peptide, said modified gene under the control of regulatory sequences directing expression of said antigen in said cell,
    wherein said effective amount is sufficient to permit the cell to accumulate antigen in the cytoplasm, process the antigen for display on the surface of said cell, whereby said antigen interacts with MHC I molecules and induces a primarily cellular immune response.

2. The method according to claim 1 wherein said HSV is HSV type 1.

3. The method according to claim 1 wherein said HSV is HSV type 2.

4. The method according to claim 1, wherein said modified gene encodes said HSV gD antigen lacking a functional cell membrane retention region.

5. The method according to claim 1, wherein said modified gene encodes said HSV gD antigen which contains a functional cell membrane retention region.

6. The method according to claim 1, wherein said modified gene is delivered in association with a polynucleotide function enhancer.

7. The method according to claim 6, wherein said enhancer is bupivacaine.

8. A method of enhancing the humoral immune response of a mammalian subject to a Herpes Simplex Virus (HSV) glycoprotein D (gD) antigen, comprising
    delivering to a mammalian cell an effective amount of a modified gene encoding an HSV gD antigen having a functional signal peptide region but lacking a functional cell membrane retention region, said modified gene under the control of regulatory sequences directing expression of said antigen in said cell,
    wherein said gD antigen is produced in the cytoplasm and secreted from said cell and interacts with antigen presenting cells to induce a humoral immune response.

9. The method according to claim 8 wherein said HSV is HSV type 1.

10. The method according to claim 8 wherein said HSV is HSV type 2.

11. The method according to claim 8, wherein said modified gene is delivered in association with a polynucleotide function enhancer.

12. The method according to claim 11, wherein said enhancer is bupivacaine.

13. A method of enhancing the immune response of a mammalian subject to a Herpes Simplex Virus (HSV) glycoprotein D (gD) antigen, said method comprising:
  (a) delivering to a cell of said subject a modified gene encoding a first HSV gD antigen lacking a functional native signal peptide, said modified gene under the control of regulatory sequences directing expression of said antigen in said cell; and
  (b) delivering to a cell of said subject a modified gene encoding a second HSV gD antigen lacking a functional cell membrane retention region, said modified gene under the control of regulatory sequences directing expression of said antigen in said cell, whereby the expressed antigen is secreted.

14. The method according to claim 13 wherein said HSV is HSV type 1.

15. The method according to claim 13 wherein said HSV is HSV type 2.

16. The method according to claim 13, wherein said gD antigen of step (a) is an HSV type 1 gD and said gD antigen of step (b) is an HSV type 2 gD.

17. The method according to claim 13, wherein said gD antigen of step (b) is an HSV type 1 gD and said gD antigen of step (a) is an HSV type 2 gD.

18. The method according to claim 13, further comprising performing step (a) prior to step (b).

19. The method according to claim 13, further comprising performing step (b) prior to step (a).

20. The method according to claim 13, comprising performing steps (a) and (b) simultaneously.

21. The method according to claim 18, comprising administering said modified gene in association with an agent that facilitates polynucleotide uptake by a cell.

22. The method according to claim 21, wherein said agent is bupivacaine.

23. A pharmaceutical composition comprising:
  (a) a modified gene encoding a Herpes Simplex Virus (HSV) glycoprotein D (gD) antigen lacking a functional native signal peptide, said modified gene under the control of regulatory sequences directing expression of said antigen in a cell;
  (b) a pharmaceutically acceptable carrier; and
  (c) an optional agent that facilitates polynucleotide uptake by a cell.

24. The composition according to claim 23 wherein said optional agent is bupivacaine.

25. The composition according to claim 23 wherein said HSV is HSV type 1.

26. The composition according to claim 23 wherein said HSV is HSV type 2.

27. The composition according to claim 26, wherein said gD gene comprises the sequence of FIG. 2 SEQ ID NO:1 having a deletion occurring within the nucleotide sequence spanning nucleotides 268 through 342 thereof.

28. The composition according to claim 27 wherein said deletion spans a nucleotide sequence of FIG. 2 SEQ ID NO:1 selected from the group consisting of:
  (a) nucleotides 268 through 286;
  (b) nucleotides 268 through 296;
  (c) nucleotides 268 through 306
  (d) nucleotides 268 through 316;
  (e) nucleotides 268 through 326; and
  (f) nucleotides 269 through 336.

29. A pharmaceutical composition comprising:
  (a) a modified gene encoding a Herpes Simplex Virus (HSV) glycoprotein D (gD) antigen lacking a functional cell membrane retention region, said modified gene under the control of regulatory sequences directing expression of said antigen in a cell;
  (b) a pharmaceutically acceptable carrier; and
  (c) an optional agent that facilitates polynucleotide uptake by a cell.

30. The composition according to claim 29 wherein said optional agent is bupivacaine.

31. The composition according to claim 29 wherein said HSV is HSV type 1.

32. The composition according to claim 29 wherein said HSV is HSV type 2.

33. The composition according to claim 32, wherein said gD gene comprises the sequence of FIG. 2 SEQ ID NO:1 having a deletion occurring within the nucleotide sequence spanning nucleotides 1247 though 1446 thereof.

34. The composition according to claim 32 wherein said deletion spans a nucleotide sequence of FIG. 2 SEQ ID NO:1 selected from the group consisting of:
  (a) nucleotides 1249 through 1446;
  (b) nucleotides 1267 through 1446;
  (c) nucleotides 1287 through 1446;
  (d) nucleotides 1306 through 1446;
  (e) nucleotides 1327 through 1446;
  (f) nucleotides 1347 through 1446;
  (g) nucleotides 1367 through 1446;
  (h) nucleotides 1387 through 1446;
  (i) nucleotides 1407 through 1446; and
  (j) nucleotides 1427 through 1446.

\* \* \* \* \*

SEQUENCE LISTING

<160> NUMBER OF SEQ ID NOS: 2

<210> SEQ ID NO 1
<211> LENGTH: 1635
<212> TYPE: DNA
<213> ORGANISM: Herpes simplex virus type 2
<220> FEATURE:
<221> NAME/KEY: CDS
<222> LOCATION: (268)..(1446)

<400> SEQUENCE: 1

```
cttgggggg gggggaaga aactaaaaac acatcaagcc cacaacccat cccacaaggg      60
gggttatggc ggaccaccg caccaccata ctccgattcg accacatatg caaccaaatc    120 accccccagag gggaggttcc atttttacga ggaggaggag tataatagag tctttgtgtt   180
taaaacccgg ggtcggtgtg gtgttcggtc ataagctgca ttgcgaacca ctagtcgccg   240 ttttcgtgt gcatcgcgta tcacggc atg ggg cgt ttg acc tcc ggc gtc ggg   294
                              Met Gly Arg Leu Thr Ser Gly Val Gly
                              1               5 acg gcg gcc ctg cta gtt gtc gcg gtg gga ctc cgc gtc gta tgc gcc   342
Thr Ala Ala Leu Leu Val Val Ala Val Gly Leu Arg Val Val Cys Ala
 10              15                  20                  25 aaa tac gcc tta gca gac ccc tcg ctt aag atg gcc gat ccc aat cga   390
Lys Tyr Ala Leu Ala Asp Pro Ser Leu Lys Met Ala Asp Pro Asn Arg
             30                  35                  40 ttt cgc ggg aag aac ctt ccg gtt ttg gac cag ctg acc gac ccc ccc   438
Phe Arg Gly Lys Asn Leu Pro Val Leu Asp Gln Leu Thr Asp Pro Pro
         45                  50                  55 ggg gtg aag cgt gtt tac cac att cag ccg agc ctg gag gac ccg ttc   486
Gly Val Lys Arg Val Tyr His Ile Gln Pro Ser Leu Glu Asp Pro Phe
     60                  65                  70 cag ccc ccc agc atc ccg atc act gtg tac tac gca gtg ctg gaa cgt   534
Gln Pro Pro Ser Ile Pro Ile Thr Val Tyr Tyr Ala Val Leu Glu Arg
 75                  80                  85 gcc tgc cgc agc gtg ctc cta cat gcc cca tcg gag gcc ccc cag atc   582
Ala Cys Arg Ser Val Leu Leu His Ala Pro Ser Glu Ala Pro Gln Ile
 90                  95                 100                 105 gtg cgc ggg gct tcg gac gag gcc cga aag cac acg tac aac ctg acc   630
Val Arg Gly Ala Ser Asp Glu Ala Arg Lys His Thr Tyr Asn Leu Thr
             110                 115                 120 atc gcc tgg tat cgc atg gga gac aat tgc gct atc ccc atc acg gtt   678
Ile Ala Trp Tyr Arg Met Gly Asp Asn Cys Ala Ile Pro Ile Thr Val
         125                 130                 135 atg gaa tac acc gag tgc ccc tac aac aag tcg ttg ggg gtc tgc ccc   726
Met Glu Tyr Thr Glu Cys Pro Tyr Asn Lys Ser Leu Gly Val Cys Pro
     140                 145                 150 atc cga acg cag ccc cgc tgg agc tac tat gac agc ttt agc gcc gtc   774
Ile Arg Thr Gln Pro Arg Trp Ser Tyr Tyr Asp Ser Phe Ser Ala Val
 155                 160                 165 agc gag gat aac ctg gga ttc ctg atg cac gcc ccc gcc ttc gag acc   822
Ser Glu Asp Asn Leu Gly Phe Leu Met His Ala Pro Ala Phe Glu Thr
170                 175                 180                 185 gcg ggt acg tac ctg cgg cta gtg aag ata aac gac tgg acg gag atc   870
Ala Gly Thr Tyr Leu Arg Leu Val Lys Ile Asn Asp Trp Thr Glu Ile
             190                 195                 200 aca caa ttt atc ctg gag cac cgg gcc cgc gcc tcc tgc aag tac gct   918
Thr Gln Phe Ile Leu Glu His Arg Ala Arg Ala Ser Cys Lys Tyr Ala
         205                 210                 215 ctc ccc ctg cgc atc ccc ccg gca gcg tgc ctc acc tcg aag gcc tac   966
```

-continued

```
                Leu Pro Leu Arg Ile Pro Pro Ala Ala Cys Leu Thr Ser Lys Ala Tyr
                            220                 225                 230 caa cag ggc gtg acg gtc gac agc atc ggg atg tta ccc cgc ttt atc          1014
Gln Gln Gly Val Thr Val Asp Ser Ile Gly Met Leu Pro Arg Phe Ile
235                 240                 245 ccc gaa aac cag cgc acc gtc gcc cta tac agc tta aaa atc gcc ggg          1062
Pro Glu Asn Gln Arg Thr Val Ala Leu Tyr Ser Leu Lys Ile Ala Gly
250                 255                 260                 265 tgg cac ggc ccc aag ccc ccg tac acc agc acc ctg ctg ccg ccg gag          1110
Trp His Gly Pro Lys Pro Pro Tyr Thr Ser Thr Leu Leu Pro Pro Glu
                270                 275                 280 ctg tcc gac acc acc aac gcc acg caa ccc gaa ctc gtt ccg gaa gac          1158
Leu Ser Asp Thr Thr Asn Ala Thr Gln Pro Glu Leu Val Pro Glu Asp
            285                 290                 295 ccc gag gac tcg gcc ctc tta gag gat ccc gcc ggg acg gtg tct tcg          1206
Pro Glu Asp Ser Ala Leu Leu Glu Asp Pro Ala Gly Thr Val Ser Ser
        300                 305                 310 cag atc ccc cca aac tgg cac atc ccg tcg atc cag gac gtc gcg ccg          1254
Gln Ile Pro Pro Asn Trp His Ile Pro Ser Ile Gln Asp Val Ala Pro
315                 320                 325 cac cac gcc ccc gcc gcc ccc agc aac ccg ggc ctg atc atc ggc gcg          1302
His His Ala Pro Ala Ala Pro Ser Asn Pro Gly Leu Ile Ile Gly Ala
330                 335                 340                 345 ctg gcc ggc agt acc ctg gcg gcg ctg gtc atc ggc ggt att gcg ttt          1350
Leu Ala Gly Ser Thr Leu Ala Ala Leu Val Ile Gly Gly Ile Ala Phe
                350                 355                 360 tgg gta cgc cgc cgc gct cag atg gcc ccc aag cgc cta cgt ctc ccc          1398
Trp Val Arg Arg Arg Ala Gln Met Ala Pro Lys Arg Leu Arg Leu Pro
            365                 370                 375 cac atc cgg gat gac gac gcg ccc ccc tcg cac cag cca ttg ttt tac          1446
His Ile Arg Asp Asp Asp Ala Pro Pro Ser His Gln Pro Leu Phe Tyr
        380                 385                 390 tagaggagtt tccccgttcc cgtgtacctc tgggcccgtg tgggagggtg gccggggtat          1506
ttgggtggga cttggactcc gcataaaggg agtctcgaag gagggaaact aggacagttc          1566
ataggccggg agcgtggggc gcgcaccgcg tcccgacgat tagccaccgc gcccacagcc          1626
acctcgacc                                                                   1635

<210> SEQ ID NO 2
<211> LENGTH: 393
<212> TYPE: PRT
<213> ORGANISM: Herpes simplex virus type 2

<400> SEQUENCE: 2

Met Gly Arg Leu Thr Ser Gly Val Gly Thr Ala Ala Leu Leu Val Val
1               5                   10                  15

Ala Val Gly Leu Arg Val Val Cys Ala Lys Tyr Ala Leu Ala Asp Pro
                20                  25                  30

Ser Leu Lys Met Ala Asp Pro Asn Arg Phe Arg Gly Lys Asn Leu Pro
            35                  40                  45

Val Leu Asp Gln Leu Thr Asp Pro Pro Gly Val Lys Arg Val Tyr His
        50                  55                  60

Ile Gln Pro Ser Leu Glu Asp Pro Phe Gln Pro Ser Ile Pro Ile
65                  70                  75                  80

Thr Val Tyr Tyr Ala Val Leu Glu Arg Ala Cys Arg Ser Val Leu Leu
                85                  90                  95

His Ala Pro Ser Glu Ala Pro Gln Ile Val Arg Gly Ala Ser Asp Glu
            100                 105                 110
```

```
Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                     150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
            275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro
                325                 330                 335

Ser Asn Pro Gly Leu Ile Ile Gly Ala Leu Ala Gly Ser Thr Leu Ala
            340                 345                 350

Ala Leu Val Ile Gly Gly Ile Ala Phe Trp Val Arg Arg Arg Ala Gln
        355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390
```